United States Patent
Ashikawa et al.

(10) Patent No.: US 8,604,030 B2
(45) Date of Patent: Dec. 10, 2013

(54) FUSED PIPERIDINE COMPOUND AND PHARMACEUTICAL CONTAINING SAME

(75) Inventors: Masanori Ashikawa, Tokyo (JP); Toshiharu Morimoto, Tokyo (JP); Hajime Yamada, Tokyo (JP); Shunji Takemura, Tokyo (JP); Tatsuaki Nishiyama, Tokyo (JP); Takeshi Doi, Tokyo (JP); Hiroyuki Ishiwata, Tokyo (JP)

(73) Assignee: Kowa Company, Ltd., Nagoya-Shi, Aichi (JP)

( * ) Notice: Subject to any disclaimer, the term of this patent is extended or adjusted under 35 U.S.C. 154(b) by 146 days.

(21) Appl. No.: 13/260,711

(22) PCT Filed: Mar. 25, 2010

(86) PCT No.: PCT/JP2010/055260
§ 371 (c)(1), (2), (4) Date: Dec. 21, 2011

(87) PCT Pub. No.: WO2010/110380
PCT Pub. Date: Sep. 30, 2010

(65) Prior Publication Data
US 2012/0108581 A1    May 3, 2012

(30) Foreign Application Priority Data

Mar. 27, 2009    (JP) ................... 2009-079544
Apr. 3, 2009    (JP) ................... 2009-091484

(51) Int. Cl.
| A61K 31/5377 | (2006.01) |
| A61K 31/4706 | (2006.01) |
| A61K 31/47 | (2006.01) |
| C07D 215/08 | (2006.01) |
| C07D 413/12 | (2006.01) |
| C07D 215/233 | (2006.01) |

(52) U.S. Cl.
USPC ........ 514/235.2; 546/160; 546/156; 544/128; 514/312; 514/313

(58) Field of Classification Search
None
See application file for complete search history.

(56) References Cited

U.S. PATENT DOCUMENTS

2013/0172345 A1*    7/2013    Ashikawa et al. ......... 514/235.2

FOREIGN PATENT DOCUMENTS

| EP | 0 992 496 A1 | 4/2000 |
| WO | WO 2004/034985 A2 | 4/2004 |
| WO | WO 2004/034985 A3 | 4/2004 |
| WO | WO 2005/097806 A1 | 10/2005 |
| WO | WO 2005097806 A1 * | 10/2005 |
| WO | WO 2006/040318 A2 | 4/2006 |
| WO | WO 2006/040318 A3 | 4/2006 |
| WO | WO 2006/094292 A2 | 9/2006 |
| WO | WO 2006/094292 A3 | 9/2006 |
| WO | WO 2009/041072 A1 | 4/2009 |
| WO | WO 2009041072 A1 * | 4/2009 |

OTHER PUBLICATIONS

PCT Application No. PCT/JP2010/055260, International Search Report, dated Apr. 20, 2010, 8 pages.

* cited by examiner

*Primary Examiner* — Jeffrey S. Lundgren
*Assistant Examiner* — Michael Schmitt
(74) *Attorney, Agent, or Firm* — Kilpatrick Townsend & Stockton LLP

(57) ABSTRACT

The present invention provides a low molecular weight compound having EPO production-promoting action and/or hemoglobin production-promoting action. The present invention relates to a fused piperidine compound represented by the following general formula (1):

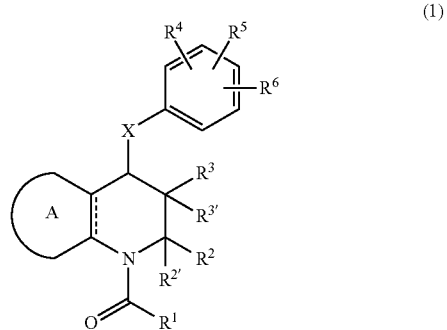

(wherein, ring A represents a $C_{10-14}$ aryl group or 5- to 10-membered heterocyclic group, X represents $N-R^7$, a sulfur atom or an oxygen atom, $R^1$, $R^2$, $R^{2'}$, $R^3$ and $R^{3'}$ independently represent a hydrogen atom, $C_{1-6}$ alkyl group or $C_{3-6}$ cycloalkyl group, and $R^4$, $R^5$ and $R^6$ independently represent a hydrogen atom or halogen atom), or a salt thereof, or a solvate thereof.

13 Claims, No Drawings

FUSED PIPERIDINE COMPOUND AND PHARMACEUTICAL CONTAINING SAME

TECHNICAL FIELD

The present invention, relates to a fused piperidine compound having erythropoietin production-promoting action and/or hemoglobin production-promoting action. More particularly, the present invention relates to a novel fused piperidine compound use for prevention and/or treatment of diseases caused by decreased erythropoietin production such as anemia.

BACKGROUND ART

Erythropoietin (EPO) is a glycoprotein hormone that is involved in the maturation and differentiation of erythroblast precursor cells into mature erythrocytes, and is a naturally-occurring monomer polypeptide composed of 165 amino acids (Non-Patent Document 1).

Human EPO is essential for proliferation and differentiation of erythrocytes, and is useful for the treatment of blood diseases characterized by a decrease in erythrocyte production. Clinically, EPO is used for the treatment of anemia, in chronic renal failure (CRF) patients, autologous transfusion and anemia of prematurity, (Non-Patent Documents 2 to 4), as well as in AIDS patients and patients undergoing chemotherapy for cancer (Non-Patent Document 5). In addition, EPO has also been recognized as being effective in chronic anemia.

Although EPO is primarily produced in the kidneys in adults, it is also produced in astrocytes and neurons of the central nervous system, and EPO and EPO receptors have also been discovered in capillaries of the boundary between the brain and the peripheral nervous system. Moreover, systemic administration of EPO has also been reported to reduce the loss of neuron cells in response to cerebral and spinal ischemia, mechanical trauma, epilepsy, excitotoxicity or neuritis by passing through the blood-brain barrier (Non-Patent Documents 6 to 10).

During treatment using proteins in the manner of EPO, problems are encountered such as the short plasma half-life as a result of being susceptible to decomposition by proteases (Non-Patent Documents 11 and 12), and the need to frequently perform intravenous injection in order to maintain an effective therapeutic concentration in the circulation. In addition, although subcutaneous injection may be used as an alternative administration route to intravenous injection, although sustained-release effects are obtained due to the slow rate of absorption from the administration site, plasma concentration is significantly lower than that in the case of intravenous injection. Therefore, the number of injections required to demonstrate an equivalent therapeutic effect is similar to that in the case of intravenous injection, thereby resulting in a burden on patients. In addition, since human serum EPO is a glycoprotein that has a complex sugar chain structure bonded to the surface of the EPO resulting in diverse and wide-ranging glycosylation, it demonstrates an absence of size uniformity, thereby resulting in the problem of recombinant human EPO being unable to be used to produce human serum EPO with good reproducibility.

Thus, there is a need in this technical field for a method and compound, not only EPO having low bioavailability in the treatment of diseases caused by decreased EPO production, including anemia as previously described, but also that increases endogenous EPO.

On the other hand, the amount of EPO produced is known to be controlled according to oxygen concentration through a transcription factor in the form of hypoxia-inducible factor (HIF) (Non-Patent Document 13). Namely, in a normal air atmosphere, although production of EPO is not promoted since an HIF sub-unit (HIF-1α), having a proline residue hydroxylated by 2-oxoglutarate dioxygenase, is decomposed by the ubiquitin proteasome system, under hypoxic conditions, hydroxylation of the proline residue of HIF-1α by 2-oxoglutarate deoxygenase is inhibited, thereby resulting in translocation of the stabilized HIF-1α from the cytoplasm to the nucleus, formation of a dimer with HIF-1β, and promotion of transcription as a result of the dimer bonding to the hypoxia-responsible element (HRE) of the EPO gene, thereby leading to promotion of EPO production.

Enzyme inhibitors of HIF prolyl hydroxylase such as 2-oxoglutarate deoxygenase using this EPO production mechanism have been reported to be used as EPO production promoters (Patent Documents 1 to 4).

However, genes for which expression is controlled by HIF include not only the gene that encodes EPO, but also the gene that encodes vascular endothelial growth factor (VEGF). VEGF has an action that promotes angiogenesis, and has been reported to be able to cause exacerbation of malignant tumors mediated by this function (Non-Patent Documents 14 and 15). In addition, since anemia is also induced by chemotherapy for the treatment of cancer, and anemia drugs can also be considered for administration to cancer patients undergoing such chemotherapy (Non-Patent Document 5), compounds having an action that inhibits the activity of HIF prolyl hydroxylase and have the potential to also promote expression of VEGF and the like that exacerbate cancer also include this risk.

Production of EPO is controlled by a promoter located on the 5'-side of EPO and an enhancer located on the 3'-side, and HIF is thought to promote production of EPO by bonding to an HRE sequence within the enhancer. In addition, GATA-2, NFκB and the like are also known to control EPO production (Non-Patent Documents 16 and 17), and promotion of EPO production is thought to be able to be achieved by a mechanism other than inhibition of the activity of HIF prolyl hydroxylase. On the basis thereof, a compound having an action that promotes EPO production without depending on inhibition of the activity of HIF prolyl hydroxylase is thought to be useful for the treatment of anemia.

In addition, although EPO promotes proliferation and differentiation of erythroblast precursor cells as described above, a compound having an action that promotes maturation and differentiation of erythroblast precursor cells without involving the production of EPO would also be useful as a drug for the treatment of anemia. Although compounds have been reported that have activity that enhances the erythrocyte proliferation promoting action of EPO and have an inhibitory action against hematopoietic cell phosphatase catalyzing dephosphorylation, which is one of the important control mechanisms of EPO signaling (Patent Documents 5 to 7), their activity cannot always be said to be adequate. In addition, although synthetic peptides called hematide have been reported that act on EPO receptors (Non-Patent Document 18), they are required to be administered at a high dosage in order to express activity equivalent to that of EPO, thereby resulting in the problem of being unsuitable for oral administration.

Thus, a low molecular weight drug for the treatment of anemia that enables oral administration and has both EPO production-promoting action and hemoglobin production-promoting action is thought to be useful for treatment of anemia in the future.

On the other hand, although compounds having a fused piperidine backbone relating to the present invention have been disclosed, including a CRTH2 inhibitor effective against inflammatory diseases (Patent Documents 8 and 9), a G protein-coupled receptor inhibitor effective for conditions such as heart failure (Patent Document 10), and a cholesterol transport protein inhibitor effective against diseases such as arteriosclerosis (Patent Documents 11 and 12), none of these publications contains descriptions or suggestions relating to EPO production-promoting action, hemoglobin production-promoting action or treatment of anemia using these compounds.

In addition, Patent Document 13 discloses a cholesterol transport protein inhibitor effective against diseases such as arteriosclerosis represented by the following general formula (a) and the compound of Example 1:

[Chemical Formula 1]

General formula (a)

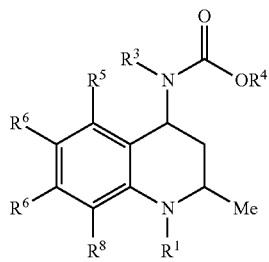

Example 1

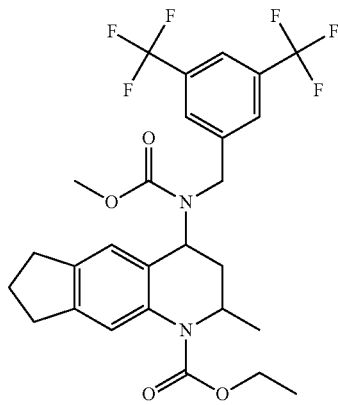

(wherein, $R^5$ and $R^6$, $R^6$ and $R^7$ or $R^7$ and $R^8$ together may form a 4- to 8-membered saturated, partially saturated or unsaturated ring that may be composed of 1 to 3 heteroatoms selected from the group consisting of a nitrogen atom, sulfur atom and oxygen atom).

In addition, Patent Document 14 discloses a proton pump inhibitor effective against gastric ulcers and the like represented by the following general formula (b) and the compound of Example 5:

[Chemical Formula 2]

General formula (b)

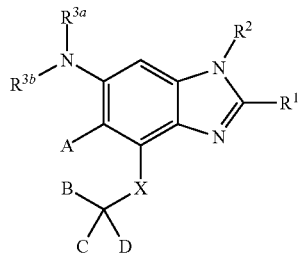

Example 5

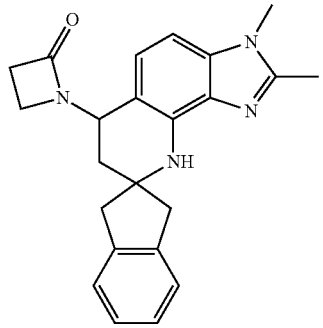

(wherein, A and B together may form a $CH_2$—$CH_2$ group, and X represents —NH— or —O—).

In addition, in Non-Patent Document 19, although the following compound (c):

[Chemical Formula 3]

Compound (c)

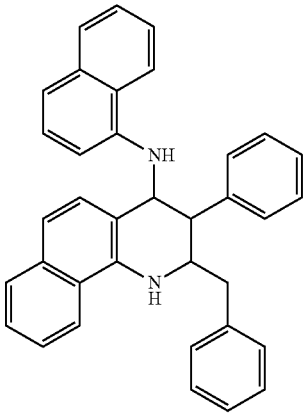

is synthesized based on its interest in terms of organic synthesis chemistry, there is no description relating to its biological activity. However, the compounds described in these publications are different from compounds of the present invention in terms of substituents of tricyclic tetrahydroxyquinoline.

In addition, Patent Document 15 discloses an STAT6 inhibitor effective against inflammatory diseases represented by the following general formula (d):

[Chemical Formula 4]

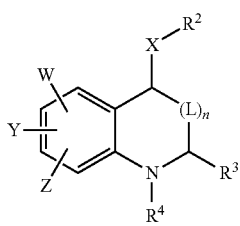

General formula (d)

(wherein, L represents $CH_2$, O or S, n represents 0 or 1, and W, Y and Z may form a methylenedioxy group). However, this publication does not specifically disclose the tricyclic compound of the present invention. Moreover, this publication does not contain any description or suggestion relating to EPO production-promoting action or hemoglobin expression-promoting action.

PRIOR ART DOCUMENTS

Patent Documents

Patent Document 1: Japanese Unexamined Patent Publication (Kokai) No. 2006-137763
Patent Document 2: WO2003/53997 pamphlet
Patent Document 3: WO2005/11696 pamphlet
Patent Document 4: WO2007/38571 pamphlet
Patent Document 5: Japanese Patent Domestic Publication (Kohyo) No. 2000-536365
Patent Document 6: Japanese Unexamined Patent Publication No. H11-171774
Patent Document 7: Japanese Unexamined Patent Publication No. 2002-275159
Patent Document 8: WO2004/32848 pamphlet
Patent Document 9: WO2005/100321 pamphlet
Patent Document 10: Japanese Unexamined Patent Publication No. 2003-321472
Patent Document 11: WO2005/95395 pamphlet
Patent Document 12: WO2005/97806 pamphlet
Patent Document 13: EP00992496
Patent Document 14: WO2008/151927 pamphlet
Patent Document 15: WO2002/79165 pamphlet Non-Patent Documents Non-Patent Document 1: Lin F-K, et al., Proc. Natl. Acad. Sci. USA, 82: 7580-7584 (1985)
Non-Patent Document 2: Eschbach J W, et al., N. Engl. J. Med., 316: 73-78 (1987)
Non-Patent Document 3: Eschbach J W, et al., Ann. Intern. Med., 111: 992 (1989)
Non-Patent Document 4: Lim V S, et al., Ann. Intern. Med., 110: 108-114 (1989)
Non-Patent Document 5: Danna R P, at al., Erythropoietin in Clinical Applications—An International Perspective, New York: Marcel Dekker: p 301-324 (1990)
Non-Patent Document 6: Sakanaka. M, et al., Proc. Natl. Acad. Sci. USA, 95, 4635-4640 (1998)
Non-Patent Document 7: Celik M, at al., Proc. Natl Acad. Sci. USA, 99, 2258-2263 (2002)
Non-Patent Document 8: Brines M L, at al., Proc. Natl. Acad. Sci. USA, 97, 10526-10531 (2000)
Non-Patent Document 9: Calapai G, et al., Eur. J. Pharmacol., 401: 349-356 (2000)
Non-Patent Document 10: Siren A-L, at al., Proc. Natl. Acad. Sci. USA, 98, 4044-4049 (2001)
Non-Patent Document 11: Spivack J L and Hogans B B, Blood, 73: 90 (1989)
Non-Patent Document 12: McMahon F G, et al., Blood, 76: 1718 (1990)
Non-Patent Document 13: Jelkman W, Internal Medicine, 43: 649-659 (2004)
Non-Patent Document 14: Maxwell P H, et al., Proc. Natl. Acad. Sci. USA, 94, 15, 8104-8109 (1997)
Non-Patent Document 15: Fang J, et al., Cancer Res., 61, 15, 5731-5735 (2001)
Non-Patent Document 16: Imagawa S, et al., Blood, 89, 1430-1439 (1997)
Non-Patent Document 17: La Feria K, et al., FASEB J, 16, 1811-1813 (2002)
Non-Patent Document 18: Stead R B, et al., Blood, 108, 1830-1834 (2006)
Non-Patent Document 19: Tarukdar S, et al., J. Org. Chem., 65, 3148-3153 (2000)

SUMMARY OF THE INVENTION

Problems to be Solved by the Invention

An object of the present invention is to provide a low molecular weight compound having EPO production-promoting action and/or hemoglobin production-promoting action. More particularly, an object of the present invention is to provide a pharmaceutical that is useful for the prevention and/or treatment of anemia.

Means for Solving the Problems

As a result of conducting extensive studies on compounds having an EPO production-promoting action and/or hemoglobin production-promoting action in consideration of the aforementioned circumstances, the inventors of the present invention found that a fused piperidine compound represented by the following general formula (1) promotes the production of EPO in a test using hepatocellular carcinoma cell line HepG2 cells and promotes the production of hemoglobin in a test using human proerythroblast cell line K562, thereby leading to completion of the present invention.

Namely, the present invention provides a fused piperidine compound represented by the following general formula (1):

[Chemical Formula 5]

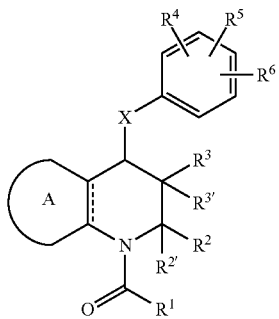

(1)

(wherein, ring A represents a $C_{10-14}$ aryl group or 5- to 10-membered heterocyclic group, X represents N—$R^7$, a sulfur atom or an oxygen atom, where $R^7$ represents a hydrogen atom or a $C_{1-6}$ alkyl group, $R^1$, $R^2$, $R^{2'}$, $R^3$ and $R^{3'}$ independently represent a group selected from the group consisting of a hydrogen atom, $C_{1-6}$ alkyl group and $C_{3-6}$ cycloalkyl group, and $R^4$, $R^5$ and $R^6$ independently represent a hydrogen atom or halogen atom), a salt thereof, or a solvate thereof.

More specifically, the present invention provides a fused piperidine compound represented by the aforementioned general formula (1), wherein the ring A moiety is selected from the group consisting of the following formulas:

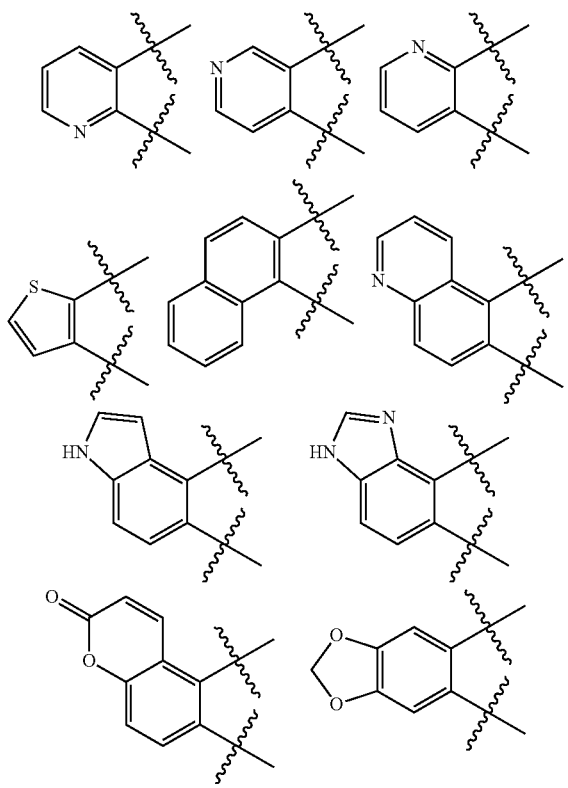

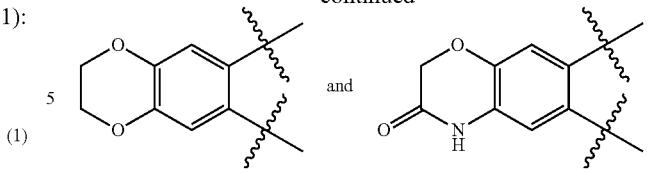

or a salt thereof, or a solvent thereof.

More specifically, the present invention provides a fused piperidine compound, wherein the compound represented by the aforementioned general formula (1) is selected from the group consisting of:

1-acetyl-4-[(4-chlorophenyl)amino]-2-methyl-3,4-dihydro-2H-[1,8]-naphthyridine (Compound 1), 1-acetyl-4-[(4-chlorophenyl)amino]-2-methyl-3,4-dihydro-2H-[1,6]-naphthyridine (Compound 2), 1-acetyl-4-[(4-chlorophenyl)amino]-2-methyl-3,4-dihydro-2H-[1,5]-naphthyridine (Compound 3), 1-(7-(4-chlorophenylamino)-5-methyl-6,7-dihydrothieno[3,2-b]pyridine-4(5H)-yl)ethanone (Compound 4), 1-acetyl-4-[(4-chlorophenyl)amino]-2-methyl-1,2,3,4-tetrahydro-benzo[h]quinoline (Compound 5), 1-[1-(4-chlorophenylamino)-3-methyl-2,3-dihydro-4,7-phenanthroline-4-(1H)-yl]ethanone (Compound 6), 6-acetyl-9-(4-chlorophenylamino)-7-methyl-6,7,8,9-tetrahydro-3H-pyrrolo[3,2-f]quinoline (Compound 7), 1-acetyl-9-[(4-chlorophenyl)amino]-7-methyl-6,7,8,9-dihydro-1H-imidazo[4,5-f]quinoline (Compound 8), 7-acetyl-10-[(4-chlorophenyl)amino]-8-methyl-7,8,9,10-tetrahydro-3H-pyrano[3,2-f]-quinolin-3-one (Compound 9), 1-[8-(4-chlorophenylamino)-6-methyl-7,8-dihydro-[1,3]dioxolo[4,5-g]quinolin-5(6H)-yl]ethanone (Compound 10), 6-acetyl-9-[(4-chlorophenyl)amino]-7-methyl-2,3,6,7,8,9-hexahydro-[1,4]dioxano[2,3-g]-quinoline (Compound 11), and 6-acetyl-9-(4-chlorophenylamino)-7-methyl-6,7,8,9-tetrahydro-2H-[1,4]oxazino[2,3-g]quinolin-3(4H)-one (Compound 12), a salt thereof, or a solvent thereof.

In addition, the present invention relates to a pharmaceutical composition comprising a one or more types of compounds consisting of a fused piperidine compound represented by the aforementioned general formula (1), a salt thereof or a solvent thereof, and a pharmaceutically acceptable carrier.

In addition, the present invention relates to a pharmaceutical composition for promoting production of EPO, comprising a fused piperidine compound represented by the aforementioned general formula (1), a salt thereof or a solvate thereof, and a pharmaceutically acceptable carrier.

In addition, the present invention relates to a pharmaceutical composition for promoting the production of hemoglobin, comprising a fused piperidine compound represented by the aforementioned general formula (1), a salt thereof or a solvate thereof, and a pharmaceutically acceptable carrier.

In addition, the present invention relates to a pharmaceutical composition for the prevention and/or treatment of anemia, comprising a fused piperidine compound represented by the aforementioned general formula (1), a salt thereof or a solvate thereof, and a pharmaceutically acceptable carrier.

In addition, the present invention relates to an EPO production promoter having as an active ingredient thereof a fused piperidine compound represented by the aforementioned general formula (1), a salt thereof or a solvate thereof.

Moreover, the present invention relates to a hemoglobin production promoter having as an active ingredient thereof a fused piperidine compound represented by the aforementioned general formula (1), a salt thereof or a solvate thereof.

In addition, the present invention relates to an anemia preventive and/or therapeutic agent having as an active ingredient thereof a fused piperidine compound represented by the aforementioned general formula (1), a salt thereof or a solvate thereof.

In addition, the present invention relates to a use of a fused piperidine compound represented by the aforementioned general formula (1), a salt thereof or a solvate thereof, for producing a preparation for promoting production of EPO.

In addition, the present invention relates to a use of a fused piperidine compound represented by the aforementioned general formula (1), a salt thereof or a solvate thereof, for producing a preparation for promoting production of hemoglobin.

In addition, the present invention relates to a use of a fused piperidine compound represented by the aforementioned general formula (1), a salt thereof or a solvate thereof, for producing a preparation for preventing and/or treating anemia.

In addition, the present invention relates to a method of promoting production of EPO, comprising administering an effective amount of a fused piperidine compound represented by the aforementioned general formula (1), a salt thereof or a solvate thereof, to a patient requiring promotion of EPO production.

In addition, the present invention relates to a method of promoting production of hemoglobin, comprising administering an effective amount of a fused piperidine compound represented by the aforementioned general formula (1), a salt thereof or a solvate thereof, to a patient requiring promotion of hemoglobin production.

In addition, the present invention relates to a method of preventing and/or treating anemia, comprising administering an effective amount of a fused piperidine compound represented by the aforementioned general formula (1), a salt thereof or a solvate thereof, to an anemia patient.

Moreover, the present invention to a method of promoting EPO production and/or method of promoting hemoglobin production in cells by contacting an effective amount of a fused piperidine compound represented by the aforementioned general formula (1), a salt thereof or a solvate thereof, with the cells. More specifically, the present invention provides a method of promoting EPO production in cells by contacting an effective amount of a fused piperidine compound selected from the aforementioned group of compounds, a salt thereof or a solvate thereof, with the cells. Here, "contact" as used in the present description refers to the addition of the compound to cells so as to regulate cell functions such as proliferation, differentiation or secretion of biologically active substances as a result of uptake of the compound by the cells or interaction on the cell surface.

Effects of the Invention

The fused piperidine compound represented by the aforementioned general formula (1), a salt thereof, or a solvate thereof, of the present invention was found to have superior EPO production-promoting action and/or hemoglobin production-promoting action, and the present invention is useful as a pharmaceutical composition for preventing and/or treating diseases in which symptoms are improved by promotion of EPO production and/or promotion of hemoglobin production (such as anemia, autologous transfusion and anemia of immaturity in chronic renal failure patients, anemia in AIDS patients and cancer patients undergoing chemotherapy, chronic anemia, iron deficiency anemia, aplastic anemia, hemolytic anemia or megaloblastic anemia). In addition, the present invention provides a preventive and/or therapeutic agent for anemia having as an active ingredient thereof a low molecular weight compound capable of being administered orally that has an EPO production-promoting action and/or hemoglobin production-promoting action.

BEST MODE FOR CARRYING OUT THE INVENTION

The following provides a detailed explanation of the present invention.

Terms used in the description of the present invention are as defined below.

A "halogen atom" as used in the present description refers to a halogeno group, and more specifically, to a fluorine atom, chlorine atom, bromine atom or iodine atom.

An "alkyl group" as used in the present invention may be linear or branched. Thus, examples of "$C_{1-6}$ alkyl groups" include linear or branched alkyl groups having 1 to 6 carbon atoms such as a methyl group, ethyl group, n-propyl group, isopropyl group, n-butyl group, isobutyl group, sec-butyl group, tert-butyl group, n-pentyl group, isopentyl group, neopentyl group, 4-methylbutyl group, 1-ethylpropyl group, n-hexyl group, isohexyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutyl group or 2-ethylbutyl group. Preferable examples consist of "$C_{1-4}$ alkyl groups".

Here, specific examples of "$C_{1-4}$ alkyl groups" include linear or branched alkyl groups having 1 to 4 carbon atoms, such as a methyl group, ethyl group, n-propyl group, isopropyl group, n-butyl group, isobutyl group, sec-butyl group or tert-butyl group.

A "$C_{3-6}$ cycloalkyl group" as used in the present description refers to a monocyclic cycloalkyl group having 3 to 6 carbon atoms such as a cyclopropyl group, cyclobutyl group, cyclopentyl group or cyclohexyl group.

An "aryl group" as used in the present description refers to a monocyclic, polycyclic or fused ring aromatic hydrocarbon group. Thus, examples of a "$C_{10-14}$ aryl group" include monocyclic, polycyclic or fused ring aromatic hydrocarbon groups having 10 to 14 carbon atoms, such as a naphthyl group, azulenyl group, anthryl group, indenyl group, fluorenyl group or phenanthryl group.

A "heterocyclic group" as used in the present description refers to a 5- to 10-membered monocyclic, polycyclic or fused ring, saturated or unsaturated heterocyclic group containing 1 to 4 heteroatoms selected from the group consisting of an oxygen atom, sulfur atom and nitrogen atom. Thus, examples of a "5- to 10-membered heterocyclic group" include a pyridyl group, pyrazyl group, pyrimidyl group, pyridazyl group, pyrrolidinyl group, imidazolidinyl group, imidazolinyl group, pyrazolidinyl group, pyrazolyl group, piperazinyl group, morpholinyl group, diazepan-1-yl group, furyl group, thienyl group, pyrrolyl group, oxazolyl group, isoxazolyl group, dihydroisoxazolyl group, thiazolyl group, isothiazolyl group, imidazolyl group, pyrazolyl group, oxadiazolyl group, thiadiazolyl group, triazolyl group, azepinyl group, oxazepinyl group, benzofuranyl group, isobenzofuranyl group, benzothienyl group, indolyl group, isoindolyl group, indazolyl group, benzoimidazolyl group, benzoxazolyl group, benzoisoxazolyl group, benzothiazolyl group, benzoisothiazolyl group, benzoxadiazolyl group, benzothiadiazolyl group, benzotriazolyl group, quinolyl group, isoquinolyl group, cinnolinyl group, quinazolinyl group, quinoxalinyl group, phthalazinyl group, naphthylidinyl group, purinyl group, pteridinyl group, 2-oxochromenyl group, 1,3-benzodioxolyl group, 1,4-benzodioxanyl group, dihydro-1,5-benzodioxepinyl group and 3-oxodihydro-1,4-benzoxazinyl group.

Other groups not defined here are in accordance with ordinary definitions.

In general formula (1), the ring A moiety is preferably an aryl group or heterocyclic ring represented by the following formulas:

[Chemical Formula 7]

In general formula (1), the "$C_{1-6}$ alkyl group" of $R^1$ is preferably a "$C_{1-4}$ alkyl group", more preferably a methyl group or ethyl group, and even more preferably a methyl group.

In general formula (1), the "$C_{3-6}$ cycloalkyl group" of $R^1$ is preferably a cyclopropyl group, cyclobutyl group, cyclopentyl group or cyclohexyl group, and more preferably a cyclopropyl group.

In general formula (1), $R^2$ and $R^{2'}$ are preferably each a $C_{1-6}$ alkyl group that may have a hydrogen atom or substituent. The "$C_{1-6}$ alkyl group" is preferably a "$C_{1-4}$ alkyl group" and more preferably a methyl group. In addition, $R^{2'}$ is preferably a hydrogen atom in the case $R^2$ is a $C_{1-6}$ alkyl group.

In general formula (1), $R^3$ and $R^{3'}$ are preferably each a hydrogen atom.

In general formula (1), the "halogen atom" of $R^4$, $R^5$ and $R^6$ is preferably a chlorine atom.

Among the fused piperidine compounds represented by general formula (1) of the present invention, in the case an asymmetric center is present at position 2 and position 4 of the piperidine ring, although the steric configuration of position 2 and position 4 may be the cis configuration or the trans configuration, the cis configuration is more preferable.

Preferable $R^1$ to $R^5$ groups in the fused piperidine compound represented by general formula (1) of the present invention can be selected by suitably combining any of the cases of $R^1$ to $R^5$ previously described.

Although the fused piperidine compound represented by general formula (1) of the present invention may have optical isomers, the present invention includes all of these optical isomers as well as racemic mixtures thereof.

The fused piperidine compound represented by general formula (1) of the present invention, a salt thereof or a solvate thereof includes not only the fused piperidine compound represented by general formula (1) of the present invention, but also includes pharmaceutically acceptable salts thereof, various types of hydrates and solvates thereof, substances having crystal polymorphism, and prodrugs of these substances.

Specific examples of pharmaceutically acceptable salts of the fused piperidine compound represented by general formula (1) of the present invention in the case of treating the compound as a basic compound include acid addition salts of inorganic acids (such as hydrochloric acid, hydrobromic acid, hydroiodic acid, sulfuric acid, nitric acid or phosphoric acid) and organic salts (such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid or glutamic acid), while in the case of treating the compound as an acidic compound, include inorganic salts (such as sodium salts, potassium salts, lithium salts, barium salts, calcium salts or magnesium salts) and organic salts (such as pyridinium salts, picolinium salts or triethylammonium salts).

Examples of solvates of the fused piperidine compound represented by general formula (1) of the present invention and pharmaceutically acceptable salts thereof include hydrates and various solvates (such as solvates of alcohols such as ethanol).

Compounds indicated in the following Tables 1 and 2, pharmaceutically acceptable salts thereof or solvates thereof are indicated as specific examples of the compound of the present invention.

TABLE 1

| Compound No. | Structural Formula | Name |
|---|---|---|
| 1 | | 1-acetyl-4-[(4-chlorophenyl)amino]-2-methyl-3,4-dihydro-2H-[1,8]-naphthyridine |
| 2 | | 1-acetyl-4-[(4-chlorophenyl)amino]-2-methyl-3,4-dihydro-2H-[1,6]-naphthyridine |
| 3 | | 1-acetyl-4-[(4-chlorophenyl)amino]-2-methyl-3,4-dihydro-2H-[1,5]-naphthyridine |
| 4 | | 1-(7-(4-chlorophenylamino)-5-methyl-6,7-dihydrothieno[3,2-b]pyridine-4(5H)-yl)ethanone |

TABLE 2

| Compound No. | Structural Formula | Name |
|---|---|---|
| 5 | | 1-acetyl-4-[(4-chlorophenyl)amino-2-methyl-1,2,3,4-tetrahydro-benzo[h]quinoline |
| 6 | | 1-[1-(4-chlorophenyl-amino)-3-methyl-2,3-dihydro-4,7-phenanthroline-4-(1H)-yl]ethanone |
| 7 | | 6-acetyl-9-(4-chlorophenyl-amino)-7-methyl-6,7,8,9-tetrahydro-3H-pyrrolo[3,2-f]quinoline |
| 8 | | 1-acetyl-9-[(4-chlorophenyl)amino]-7-methyl-6,7,8,9-dihydro-1H-imidazo[4,5-f]quinoline |
| 9 | | 7-acetyl-10-[(4-chlorophenyl)amino]-8-methyl-7,8,9,10-tetrahydro-3H-pyrano[3,2-f]-quinolin-3-one |

TABLE 2-continued

| Compound No. | Structural Formula | Name |
|---|---|---|
| 10 | | 1-[8-(4-chlorophenyl-amino)-6-methyl-7,8-dihydro-[1,3]dioxolo[4,5-g]quinolin-5(6H)-yl]ethanone |
| 11 | | 6-acetyl-9-[(4-chlorophenyl)amino]-7-methyl-2,3,6,7,8,9-hexahydro-[1,4]dioxano[2,3-g]-quinoline |
| 12 | | 6-acetyl-9-(4-chlorophenyl-amino)-7-methyl-6,7,8,9-tetrahydro-2H-[1,4]oxazino[2,3-g]quinolin-3(4H)-one |

The fused piperidine compound represented by general formula (1) of the present invention can be produced according to a known method. For example, the fused piperidine compound can be produced according to the method indicated below or a method based thereon.

[Production Method 1] Production Method of Compound in which X is NH or N-alkyl in General Formula (1)

1-1.

A compound [D] of the present invention can be produced according to the method represented by the following reaction formula:

[Chemical Formula 8]

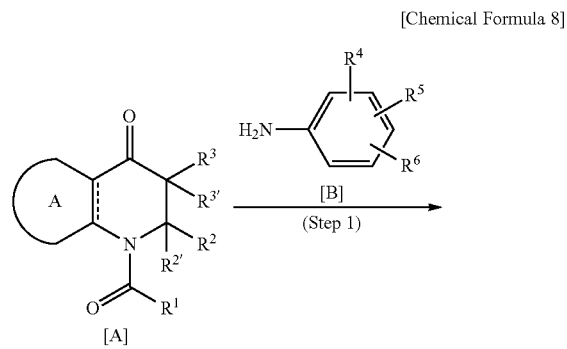

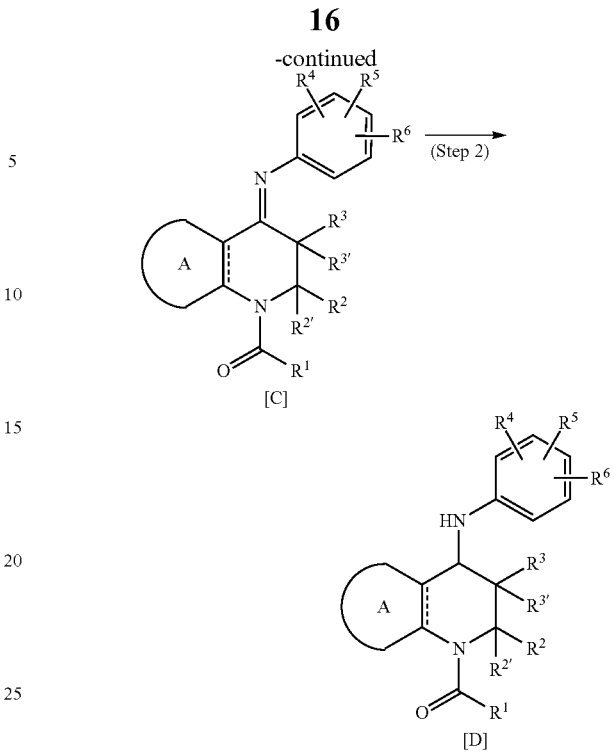

(wherein, ring A, $R^1$, $R^2$, $R^{2'}$, $R^3$, $R^{3'}$, $R^4$, $R^5$ and $R^6$ represent the same groups as previously defined).

Compound [D] can be produced by reductive amination from a 4-oxo-fused piperidine compound represented by general formula [A]. Comprehensive Organic Synthesis, 1991, vol. 8, p. 21, for example, can be referred to regarding the method for introducing an amino group by reductive amination.

(Step 1) Compound [C] can be produced by reacting Compound [A] and Compound [B] in a solvent and in the presence of acid for 5 minutes to 40 hours (and preferably, 1 hour to 18 hours) while cooling or warming. Examples of the acid include titanium tetrachloride, p-toluenesulfonic acid and trifluoroacetic acid. Examples of the solvent include organic solvents such as toluene, dichloromethane, benzene or tetrahydrofuran, and these can be used alone or in combination.

(Step 2) Compound [D] can be synthesized by reacting Compound [C] in a solvent and in the presence of a reducing agent for 5 minutes to 40 hours (and preferably, 1 hour to 18 hours) while cooling or warming. Examples of the reduction method include contact reduction with hydrogen gas using a metal catalyst such as palladium carbon, palladium black, palladium hydroxide, platinum oxide or Rainey nickel, and a method using sodium borohydride, sodium cyanoborohydride, sodium triacetoxyborohydride, zinc borohyride, borane, aluminum hydride, diisobutyl aluminum hydride or sodium-alcohol. Examples of the solvent include organic solvents such as methanol, ethanol, N,N-dimethylformamide, diethyl ether, 1,4-dioxane, tetrahydrofuran, acetic acid or ethyl acetate, and water, and these can be used alone or in combination.

In addition, in addition to carrying out step 1 and Step 2 consecutively as described above, Compound [D] can also be produced from Compound [A] by a method in which Step 1 and Step 2 are carried out all at once within the same system.

Moreover, a compound in which X is an N-alkyl can be produced from Compound [D] using a known method, such as a reductive amination reaction (porch reaction (J. Am.

Chem. Soc., 2897 (1971)), Lockart-Wallach reaction (Org. React., 301 (1949)), Eshweiler-Clark reaction (J. Am. Chem. Soc., 4571 (1933)) or amino group alkylation reaction.

1-2.

A Compound [Aa], which is a 4-oxo-fused piperidine compound used to produce Compound [D] of the present invention in which $R^{3'}$ is a hydrogen atom, can be produced in accordance with the following production method with reference to a known procedure such as that of WO 2002/53557:

[Chemical Formula 9]

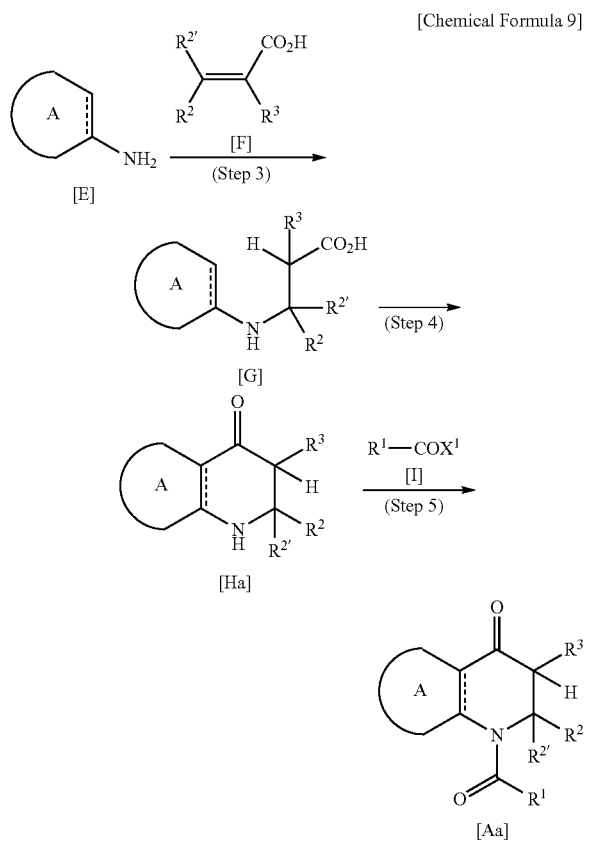

(wherein, ring A, $R^1$, $R^2$, $R^{2'}$ and $R^3$ represent the same groups as previously defined, and $X^1$ represents a leaving group).

(Step 3) Compound [G] can be produced by reacting Compound [E] and Compound [F] in a solvent for 5 minutes to 40 hours (and preferably, 1 hour to 18 hours) while warming. Examples of the solvent include organic solvents such as toluene, benzene, ethyl acetate, methyl isobutyl ketone or methyl-tert-butyl ether, and these can be used alone or in combination.

(Step 4) Compound [Ha] can be produced by reacting Compound [G] in the presence of an acid such as polyphosphoric acid for 5 minutes to 4 hours (and preferably, 1 hour to 18 hours) while warming. Examples of solvents include organic solvents such as toluene or benzene, and these can be used alone or in combination.

(Step 5) Compound [Aa] can be produced by reacting Compound [Ha] and Compound [I] in a solvent and in the presence or absence of a base for 5 minutes to 40 hours (and preferably, 1 hour to 18 hours) while cooling or warming. Examples of the base include triethylamine, N,N-diisopropylethylamine, N-methylmorpholine, N-methylpiperidine and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or dimethylformamide, and water, and these can be used alone or in combination. Here, $X^1$ in Compound [I] represents an atom or functional group that functions as a leaving group, and examples thereof include a halogen atom such as chlorine or bromine, and an acyl group such as a pivaloyl group.

1-3.

In addition, a 4-oxo-fused piperidine compound [A] used to produce Compound [D] in the present invention can be produced according to the following method with reference to, a known procedure such as that described in WO 2002/79165:

[General Formula 10]

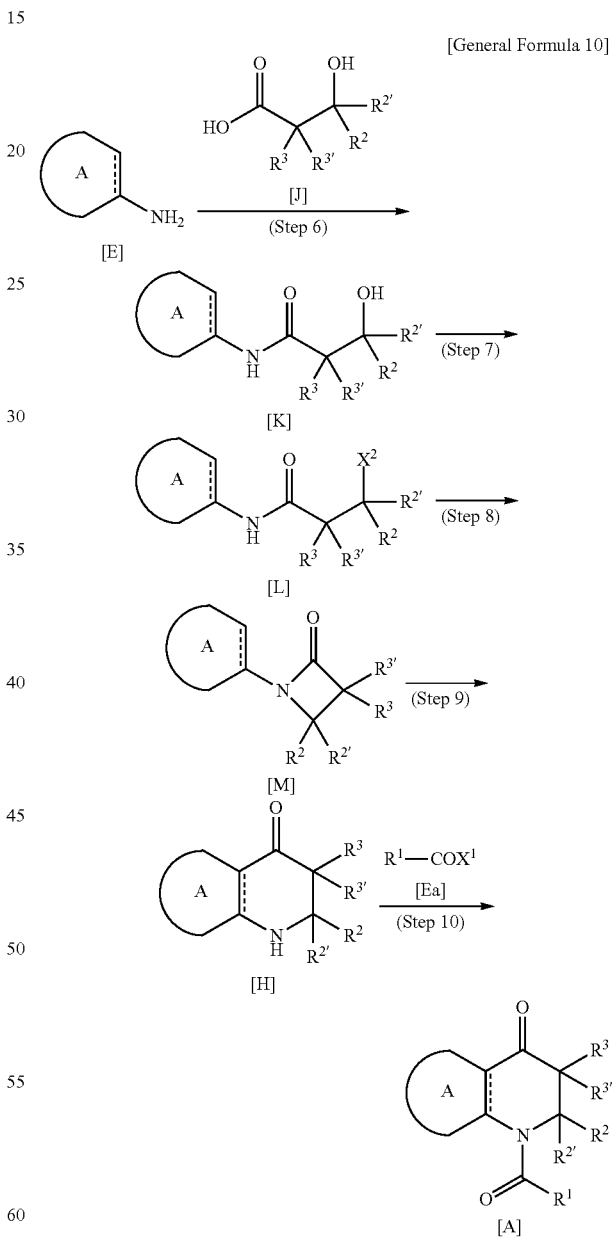

(wherein, ring A, $R^1$, $R^2$, $R^{2'}$, $R^3$ and $R^{3'}$ represent the same groups as previously defined, and $X^1$ and $X^2$ represent leaving groups).

(Step 6) Compound [K] is obtained by reacting Compound [E] with an equal or excess amount of Compound [J] in a solvent and in the presence or absence of a base for 5 minutes to 40 hours (and preferably, 1 hour to 18 hours) while cooling or warming. At this time, 1,3-dicyclohexylcarbodiimide (DCC), 1-ethyl-3-(3-dimethylaminopropyl)carbodiimide hydrochloride (WSC), oxalyl chloride or thionyl chloride can be used as a reaction reagent. Examples of the base include organic bases such as triethylamine or N,N-diisopropylethylamine, and inorganic bases such as potassium carbonate, sodium carbonate, potassium hydroxide, sodium hydroxide or lithium hydroxide. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination.

(Step 7) Compound [L] can be produced by reacting Compound [K] with an alkylsulfonyl halide, arylsulfonyl halide, alkylsulfonic acid anhydride or arylsulfonic acid anhydride in a solvent and in the presence of a base for 5 minutes to 40 hours (and preferably, 5 minutes to 18 hours) while cooling or warming. Examples of the alkylsulfonyl halide include methanesulfonyl chloride and trifluoromethanesulfonyl chloride, and examples of the arylsulfonyl halide include toluenesulfonyl chloride. Examples of the alkylsulfonic acid anhydride include methanesulfonic acid anhydride, and examples of the arylsulfonic acid anhydride include toluenesulfonic acid anhydride. Examples of the base include pyridine, triethylamine, N,N-diisopropylethylamine, N-morpholine, N-methylpiperidine and picoline. In addition, examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination.

(Step 8) Compound [M] can be produced by reacting Compound [L] in the presence of a base for 5 minutes to 40 hours (and preferably, 1 hour to 18 hours) while cooling or warming. Examples of the base include sodium hydride, potassium hydride, sodium hydroxide, potassium hydroxide and lithium hydroxide, and sodium hydroxide is preferable. Examples of solvents include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether and N,N-dimethylformamide, these can be used alone or in combination, and the solvent is preferably N,N-dimethylformamide.

(Step 9) Compound [H] can be produced by reacting Compound [M] in the presence of an acid such as trifluoromethanesulfonic acid and in a solvent for 5 minutes to 40 hours (and preferably, 1 hour to 18 hours) while cooling or warming. Examples of the solvent include toluene, dichloromethane, benzene and tetrahydrofuran, and these can be used alone or in combination.

(Step 10) Compound [A] can be produced from Compound [H] by the method described in Step 5 of Production Method 1-2.

1-4.

In addition, a Compound [Ab], in which $R^{2'}$ and $R^{3'}$ represent hydrogen atoms and $R^2$ represents —$CH_2$—$R^{3'}$ in the 4-oxo-fused piperidine compound [A] can be produced according to the following method with reference to a known procedure such as that described in Journal of the Chemical Society, Perkin Transactions 1, 1994, vol. 59, pp. 9-13:

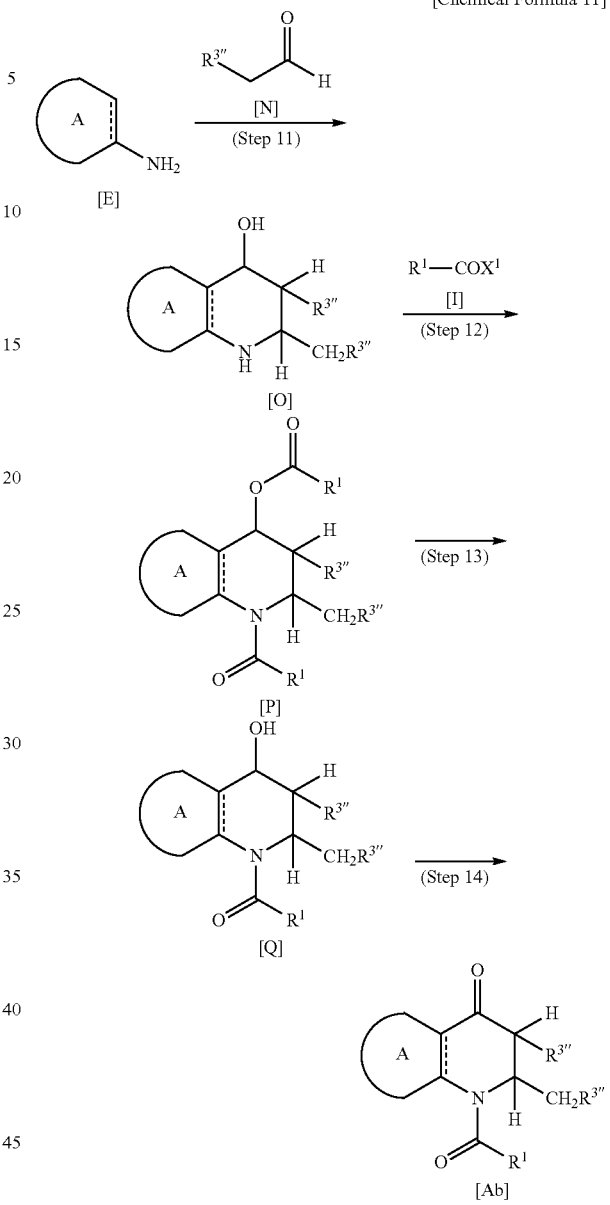

[Chemical Formula 11]

(wherein, ring A and $R^1$ represent the same groups as previously defined, $R^{3''}$ represents a hydrogen atom, alkyl group or cycloalkyl group, and $X^1$ represents a leaving group).

(Step 11) Compound [O] can be produced by reacting Compound [E] and Compound [N] (2 to 10 equivalents and preferably 3 to 4 equivalents) in a solvent and in the presence of an acid for 5 minutes to 40 hours (and preferably, 1 hour to 18 hours) while cooling or warming. Examples of the acid include inorganic acids such as hydrochloric acid, hybrobromic acid, sulfuric acid, phosphoric acid or nitric acid, and organic acids such as acetic acid, oxalic acid, citric acid, tartaric acid, maleic acid or benzoic acid. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination.

(Step 12) Compound [P] can be produced by reacting Compound [O] and Compound [I] in a solvent and in the presence or absence of a base for 5 minutes to 40 hours (and preferably, 1 hour to 18 hours) while cooling or warming. Examples of the base include pyridine, triethylamine, N,N-diisopropylethylamine, N-methylmorpholine, N-methylpiperidine and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, water and mixed solvents thereof, and these can be used alone or in combination. Here, X1 in Compound [I] represents an atom or functional group that functions as a leaving group, and examples thereof include a halogen atom such as chlorine or bromine, and an acyl group such as a pivaloyl group.

(Step 13) Compound [Q] can be produced from Compound [P] by hydrolysis with hydroxide ion or alkolyis with alkoxide. At this time, examples of base that can be used include potassium carbonate, sodium carbonate, potassium hydroxide, sodium hydroxide and lithium hydroxide, while examples of solvents that can be used include water and organic solvents such as methanol, ethanol, isopropyl alcohol, tetrahydrofuran, 1,4-dioxane or dimethoxyethane, and these can be used alone or in combination with water. The reaction temperature and reaction time are such that the reaction can be suitably carried out while cooling or warming for 5 minutes to 40 hours (and preferably, 1 hour to 18 hours).

(Step 14) Compound [Ab] is obtained by reacting Compound [Q] and an oxidizing agent in a solvent for 5 minutes to 40 hours (and preferably, 1 hour to 18 hours) while cooling or warming. Examples of the oxidizing agent include dimethylsulfoxide-oxalyl chloride, acetic anhydride, trifluoroacetic acid anhydride or DCC-triethylamine, hydrogen peroxide, tetraisopropylammonium pertenate, manganese dioxide, pyridinium chlorochromate (PCC), and potassium dichromate or potassium permanganate. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination.

1-5

Compound [Ac], in which $R^{2'}$, $R^3$ and $R^{3'}$ are hydrogen atoms in the 4-oxo-fused piperidine compound [A] used to produce Compound [D] of the present invention, can be produced according to the following production method with reference to a known procedure such as that described in WO 2005/97806:

[Chemical Formula 12]

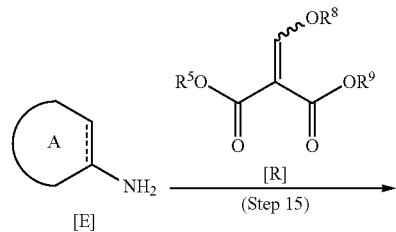

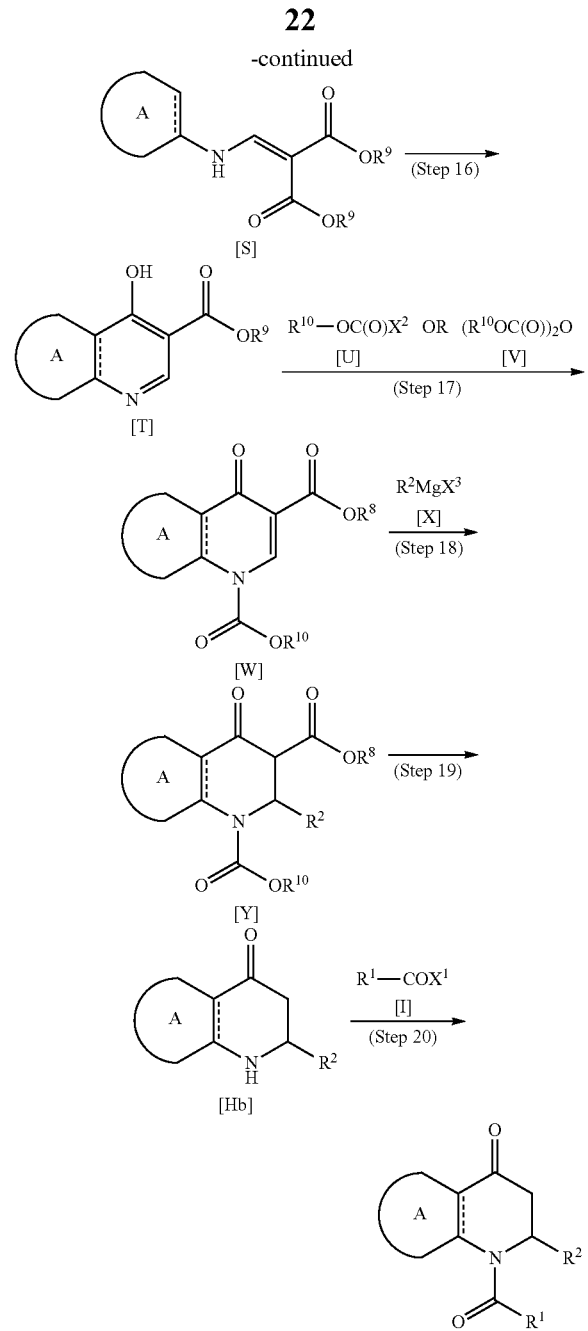

(wherein, ring A, $R^1$ and $R^2$ represent the same groups as previously defined, $R^8$ represents a hydroxyl group protecting group, $R^9$ represents a carboxyl group protecting group, $X^2$ represents a leaving group, and $X^3$ represents a halogen atom).

(Step 15) Compound [S] can be produced by reacting Compound [E] and Compound [R] in a solvent for 0.5 hours to 40 hours (and preferably, 1 hour to 18 hours) while warming. Examples of the solvent include organic solvents such as toluene, benzene or diphenyl ether, and these can be used alone or in combination.

(Step 16) Compound [T] can be produced by reacting Compound [S] in the presence or absence of a solvent for 0.1 hours to 10 hours (and preferably, 0.2 hours to 2 hours) while warming. In the case of using a solvent, examples of the solvent include organic solvents such as toluene and diphenyl ether, and these can be used alone or in combination.

(Step 17) Compound [W] can be produced by reacting Compound [T] and [U] or Compound [T] and [V] in a solvent and in the presence of a base for 1 minute to 20 hours (and preferably, 5 minutes to 10 hours) while cooling or warming. Examples of the base include pyridine, triethylamine, N,N-diisopropylethylamine, N-methylmorpholine, N-methylpiperidine and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination. Here, $X^1$ in [U] represents an atom or functional group that functions as a leaving group, and examples thereof include a halogen atom such as fluorine, chlorine or bromine, and an acyl group such as a pivaloyl group.

(Step 18) Compound [Y] can be produced by reacting Compound [W] and [X] in a solvent for 1 hour to 40 hours (and preferably, 2 hours to 18 hours) at room temperature or while cooling. A reagent conventionally used in Grignard reactions can be used for [X]. Preferable examples of the reaction solvent include a cyclic ether in the form of tetrahydrofuran and a mixed solvent or tetrahydrofuran and hexane.

(Step 19) Compound [Hb] can be obtained by carrying out ester hydrolysis by reacting Compound [Y] in a solvent and in the presence of an acid or base for 5 minutes to 8 hours (and preferably, 10 minutes to 4 hours) at room temperature or while warming, followed by carrying out a decarboxylation reaction by reacting the resulting reaction product in a solvent and in the presence or acid or base for 10 minutes to 8 hours (and preferably, 30 minutes to 5 hours) while warming. Alternatively, Compound [Hb] can be obtained by reacting Compound [Y] in a solvent and in the presence of acid or base for 30 minutes to 10 hours (and preferably, 1 hour to 5 hours). At this time, examples of acids that can be used include inorganic acids such as hydrochloric acid or sulfuric acid, and organic acids such as p-toluenesulfonic acid, trifluoroacetic acid or acetic acid. Examples of bases that can be used include potassium carbonate, sodium carbonate, potassium hydroxide, sodium hydroxide and lithium hydroxide. Examples of the solvent include water and organic solvents such as methanol, ethanol, isopropyl alcohol, tetrahydrofuran, 1,4-dioxane or dimethoxyethane, and these can be used alone or in combination with water.

(Step 20) Compound [Ac] can be produced by reacting Compound [Hb] and Compound [I] in a solvent and in the presence or absence of a base for 5 minutes to 40 hours (and preferably, 1 hour to 18 hours) while cooling or warming. Examples of the base include pyridine, triethylamine, N,N-diisopropylethylamine, N-methylmorpholine, N-methylpiperidine and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination. Here, $X^1$ in Compound [I] represents an atom or functional group that functions as a leaving group, and examples thereof include a halogen atom such as fluorine, chlorine or bromine, and an acyl group such as a pivaloyl group.

[Production Method 2] Production Method of Compound in which X is NH and N-alkyl in General Formula (1) 1-6.

Compound [D] of the present invention can also be produced according to the method represented by the following reaction formula:

[Chemical Formula 13]

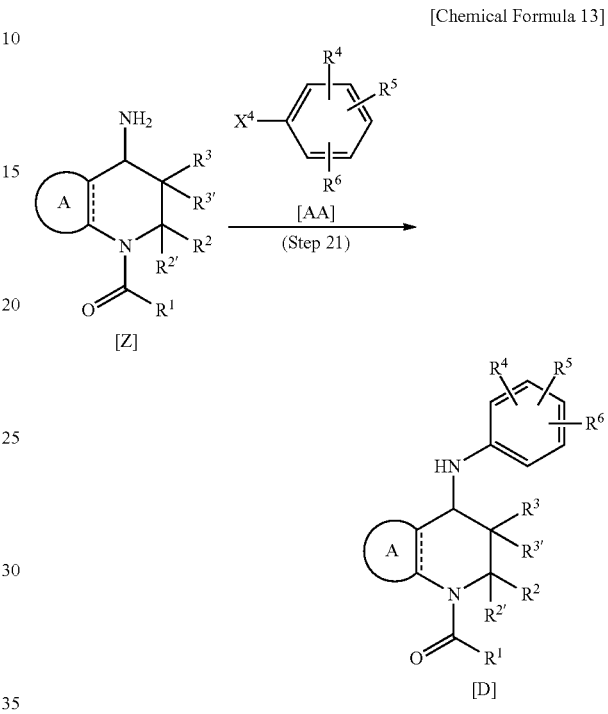

(wherein, ring A, $R^1$, $R^2$,$R^{2'}$, $R^3$,$R^{3'}$, $R^4$, $R^5$ and $R^6$ represent the same groups as previously defined, and $X^4$ represents a leaving group).

Compound [D] can be produced from the 4-amino-fused piperidine compound represented by general formula (Z) by an aromatic amination reaction using a metal. The method used to introduce an aromatic ring by an aromatic amination reaction can be carried out by referring to, for example, Angew. Chem. Int. Ed., 1998, vol. 37, p. 2046, Org. Lett., 2003, vol. 5, p. 2413, or Tetrahedron Lett., 2003, p. 1691.

(Step 21) Compound [D] can be produced by reacting Compound [Z] and Compound [AA] in a solvent, in the presence or absence of a metal and in the presence of a base for 30 minutes to 40 hours (and preferably, 1 hour to 18 hours) while cooling or warming. Examples of the base include sodium tert-butoxide, pyridine, triethylamine, cesium carbonate, potassium carbonate, potassium phosphate, potassium tert-butoxide, lithium bis(trimethylsilyl) amide and 1,8-diazobicyclo[5.4.0]undec-7-ene. Examples of the metal include copper acetate, copper oxide, copper bromide, copper iodide, tris(dibenzylideneacetone) dipalladium, palladium acetate, bis(1,5-cyclooctadiene) nickel and palladium chloride. In addition, ligands such as (R)-(+)-2,2'-bis(diphenylphosphino)-1,1'-binaphthyl, (S)-(−)-2,2'-bis(diphenylphosphino)-1,1'-binaphthyl, (±)-2,2'-bis(biphenylphosphino)-1,1'-binaphthyl, tris(o-tolyl)phosphine, 1,3-bis(diphenylphosphino)propane, tris(1-naphthyl)phosphine, tris(o-methoxyphenyl)phosphine, triphenylphosphine, 1,1'-bis(diphenylphosphino)ferrocene or o-(di-tert-butylphosphino)biphenyl are used suitably. Examples of the solvent include toluene, tetrahydrofuran, dioxane, dichloromethane, N,N-dimethylformamide and dimethoxyethane. These solvents may be used alone or in combination. Here, $X^4$ in Compound [AA] represents an atom or functional group that functions as a leaving group, and examples thereof include a halogen atom such as chlorine or bromine, and a boron-containing functional group such as a borono group.

1-7.

The 4-amino-fused piperidine compound [Z] used to produce Compound [D] of the present invention can be produced in accordance with the following production method with reference to a known procedure, such as that described in WO 2005/100321 or J. Org. Chem., 1995, vol. 60, p. 3993:

Examples of the acid include inorganic acids, organic acids and Lewis acids. Examples of inorganic acids include hydrochloric acid, hydrobromic acid, sulfuric acid, phosphoric acid, tetrafluoroboric acid, perchloric acid and periodic acid. Examples of organic acids include formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, carboxylic acids such as glycolic acid, and sulfonic acids such as methanesulfonic acid, benzenesulfonic acid, p-toluenesulfonic acid or trifluoromethanesulfonic acid. Examples of Lewis acids include aluminum halides such as aluminum chloride or

[Chemical Formula 14]

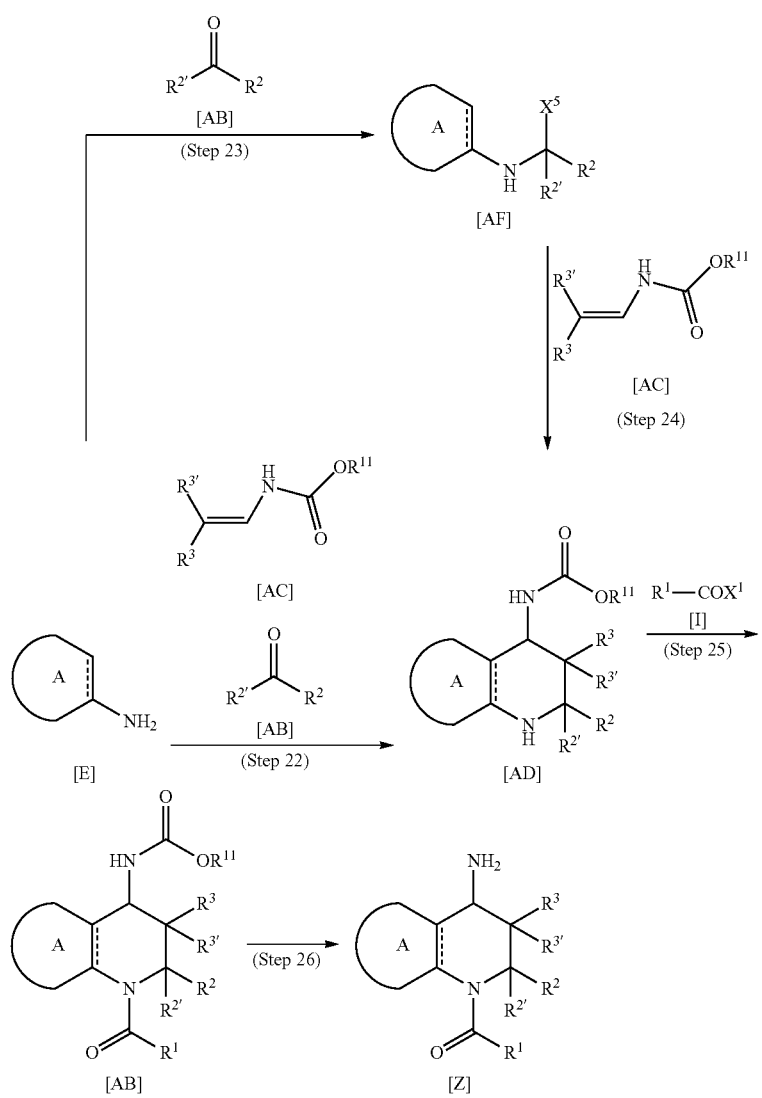

(wherein, ring A, $R^1$, $R^2$, $R^{2'}$, $R^3$ and $R^{3'}$ represent the same groups as previously defined, $X^1$ represents a leaving group, $X^5$ represents a heterocyclic compound, phenol or alcohol, and $R^{11}$ represents an alkyl group and the like).

(Step 22) Compound [AD] can be produced by reacting Compound [E], Compound [AB] and Compound [AC] in a solvent and in the presence of an acid for 1 hour to 10 hours (and preferably, 3 hours to 8 hours) while cooling or warming.

aluminum bromide, dialkyl aluminum halides such as diethyl aluminum chloride, diethyl aluminum bromide or diisopropyl aluminum chloride, trialkyl borates such as trimethyl borate, triethyl borate, tripropyl borate or tri-tert-butyl borate, trialkoxy aluminum compounds such as triethoxyaluminum, triisopropoxyaluminum or tri-tert-butoxyaluminum, titanium halides such as titanium tetrachloride, tetraalkoxy titanium compounds such as tetraisopropoxytitanium, boron halides such as boron trifluoride, boron trichloride, boron tribromide or boron trifluoride-diethyl, ether complex, and zinc halides such as zinc chloride or zinc bromide. These acids may each be used alone or two or more types may be suitably used in combination. Among these acids, sulfuric acid, hydrochloric acid, methanesulfonic acid, trifluoromethanesulfonic acid and boron trifluoride-ethyl ether complex are preferable. Examples of the solvent include aliphatic hydrocarbons such as pentane, hexane, heptane, octane, decane or cyclohexane, aromatic hydrocarbons such as benzene, toluene or xylene, halogenated hydrocarbons such as dichloromethane, 1,2-dichloroethane, chloroform, carbon tetrachloride or o-dichlorobenzene, ethers such as diethyl ether, diisopropyl ether, text-butyl methyl ether, dimethoxyethane, ethylene glycol diethyl ether, tetrahydrofuran, 1,4-dioxane, 1,3-dioxolane or cyclopentyl methyl ether, ketones such as acetone, methyl ethyl ketone, methyl isobutyl ketone or cyclohexanone, alcohols such as methanol, ethanol, 2-propanol, n-butanol, 2-ethoxyethanol or benzyl alcohol, polyvalent alcohols such as ethylene glycol, propylene glycol, 1,2-propanediol or glycerin, esters such as methyl acetate, ethyl acetate, n-butyl acetate or methyl propionate, amides such as formamide, N,N-dimethylformamide or N,N-dimethylacetoamide, sulfoxides such as dimethylsulfoxide, cyano-containing organic compounds such as acetonitrile, N-methylpyrrolidone and water. These solvents may be used alone or in combination. Furthermore, Compound [AD] can also be synthesized according to Step 23 and Step 24 by going through the imine equivalent [AF].

(Step 23) Compound [AF] can be synthesized by reacting Compound [E] and Compound [AE] with a hetero compound such as benzotriazole, purine, imidazole, 4-nitrophenol, 2-mercaptopyridine, 2-hydroxypyridine or 2-mercaptobenzothiazole, or an alcohol such as methanol, ethanol, 2-propanol, n-butanol, 2-ethoxyethanol or benzyl alcohol (and preferably, benzotriazole) in a solvent while cooling, warming or at room temperature. Examples of the solvent used include aliphatic hydrocarbons such as pentane, hexane, heptane, octane, decane or cyclohexane, aromatic hydrocarbons such as benzene, toluene or xylene, halogenated hydrocarbons such as dichloromethane, 1,2-dichloroethane, chloroform, carbon tetrachloride or o-dichlorobenzene, ethers such as diethyl ether, diisopropyl ether, text-butyl methyl ether, dimethoxyethane, ethylene glycol diethyl ether, tetrahydrofuran, 1,4-dioxane, 1,3-dioxolane or cyclopentyl methyl ether, ketones such as acetone, methyl ethyl ketone, methyl isobutyl ketone or cyclohexanone, alcohols such as methanol, ethanol, 2-propanol, n-butanol, 2-ethoxyethanol or benzyl alcohol, polyvalent alcohols such as ethylene glycol, propylene glycol, 1,2-propanediol or glycerin, esters such as methyl acetate, ethyl acetate, butyl acetate or methyl propionate, amides such as formamide, N,N-dimethylformamide or N,N-dimethylacetoamide, sulfoxides such as dimethylsulfoxide, cyano-containing organic compounds such as acetonitrile, N-methylpyrrolidone and water. These solvents may be used alone or in combination.

(Step 24) Compound [AD] can be produced by reacting Compound [AF] and Compound [AC] in a solvent and in the presence or absence of an acid for 30 minutes to 24 hours (and preferably, 1 hour to 4 hours) while cooling or warming. Examples of the acid include inorganic acids, organic acids and Lewis acids. Examples of organic acids include hydrochloric acid, hydrobromic acid, sulfuric acid, phosphoric acid, tetrafluoroboric acid, perchloric acid and periodic acid. Examples of organic acids include formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, carboxylic acids such as glycolic acid, and sulfonic acids such as methanesulfonic acid, benzenesulfonic acid, p-toluenesulfonic acid or trifluoromethanesulfonic acid. Examples of Lewis acids include aluminum halides such as aluminum chloride or aluminum bromide, dialkyl aluminum halides such as diethyl aluminum chloride, diethyl aluminum bromide or diisopropyl aluminum chloride, trialkyl borates such as trimethyl borate, triethyl borate, tripropyl borate or tri-tert-butyl borate, trialkoxy aluminum compounds such as triethoxyaluminum, triisopropoxyaluminum or tri-tert-butoxyaluminum, titanium halides such as titanium tetrachloride, tetraalkoxy titanium compounds such as tetraisopropoxytitanium, boron halides such as boron trifluoride, boron trichloride, boron tribromide or boron trifluoride-diethyl ether complex, and zinc halides such as zinc chloride or zinc bromide. These acids may be used alone or in combination. Among these acids, sulfuric acid, hydrochloric acid, methanesulfonic acid, trifluoromethanesulfonic acid and boron trifluoride-ethyl ether complex are preferable. Examples of the solvent include aliphatic hydrocarbons such as pentane, hexane, heptane, octane, decane or cyclohexane, aromatic hydrocarbons such as benzene, toluene or xylene, halogenated hydrocarbons such as dichloromethane, 1,2-dichloroethane, chloroform, carbon tetrachloride or dichlorobenzene, ethers such as diethyl ether, diisopropyl ether, tert-butyl methyl ether, dimethoxyethane, ethylene glycol diethyl ether, tetrahydrofuran, 1,4-dioxane, 1,3-dioxolane or cyclopentyl methyl ether, ketones such as acetone, methyl ethyl ketone, methyl isobutyl ketone or cyclohexanone, alcohols such as methanol, ethanol, 2-propanol, n-butanol, 2-ethoxyethanol or benzyl alcohol, polyvalent alcohols such as ethylene glycol, propylene glycol, 1,2-propanediol or glycerin, esters such as methyl acetate, ethyl acetate, n-butyl acetate or methyl propionate, amides such as formamide, N,N-dimethylformamide or N,N-dimethylacetoamide, sulfoxides such as dimethylsulfoxide, cyano-containing organic compounds such as acetonitrile, N-methylpyrrolidone and water. These solvents may be used alone or in combination.

(Step 25) Compound [AH] can be produced by reacting Compound [AD] and Compound [I] in a solvent and in the presence or absence of a base for 5 minutes to 40 hours (and preferably, 1 hour to 18 hours) while cooling or warming. Examples of the base include pyridine, triethylamine, N,N-diisopropylethylamine, N-methylmorpholine, N-methylpiperidine and picoline. Examples of the solvents include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination. Here, $X^1$ in Compound [I] represents an atom or functional group that functions as a leaving group, and examples thereof include a halogen atom such as chlorine or bromine, and an acyl group such as a pivaloyl group.

(Step 26) Compound [Z] can be synthesized by reacting Compound [AH] in a solvent and in the presence of a reducing agent or in the presence of an acid for 5 minutes to 40 hours (and preferably, 1 hour to 18 hours) while cooling, warming or at room temperature. A contact reduction reaction is carried out with hydrogen gas using palladium carbon, palladium black, palladium hydroxide, platinum oxide or Rainey nickel for the reducing agent. Examples of the acid include inorganic acids such as hydrochloric acid, hydrobromic acid, sulfuric acid, phosphoric acid, tetrafluoroboric acid, perchloric acid or periodic acid. Examples of organic acids include formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, carboxylic acids such as glycolic acid, and sulfonic acids such as methanesulfonic acid, benzenesulfonic acid, p-toluenesulfonic acid or trifluoromethanesulfonic acid. Examples of Lewis acids include aluminum halides such as aluminum chloride or aluminum bromide, dialkyl aluminum halides such as diethyl aluminum chloride, diethyl aluminum bromide or diisopropyl aluminum chloride, trialkyl borates such as trimethyl borate, triethyl borate, tripropyl borate or tri-tert-butyl borate, trialkoxy aluminum compounds such as triethoxyaluminum, triisopropoxyaluminum or tri-tert-butoxyaluminum, titanium halides such as titanium tetrachloride, tetraalkoxy titanium compounds such as tetraisopropoxytitanium, boron halides such as boron trifluoride, boron trichloride, boron tribromide or boron trifluoride-diethyl ether complex, and zinc halides such as zinc chloride or zinc bromide. Hydrochloric acid, trifluoroacetic acid and trifluoromethanesulfonic acid are preferable.

1-8.

In addition, the 4-amino-fused piperidine compound [Z] used to produce the Compound [D] of the present invention can also be produced according to the following method with reference to a known procedure such as that described in WO 2004/032848:

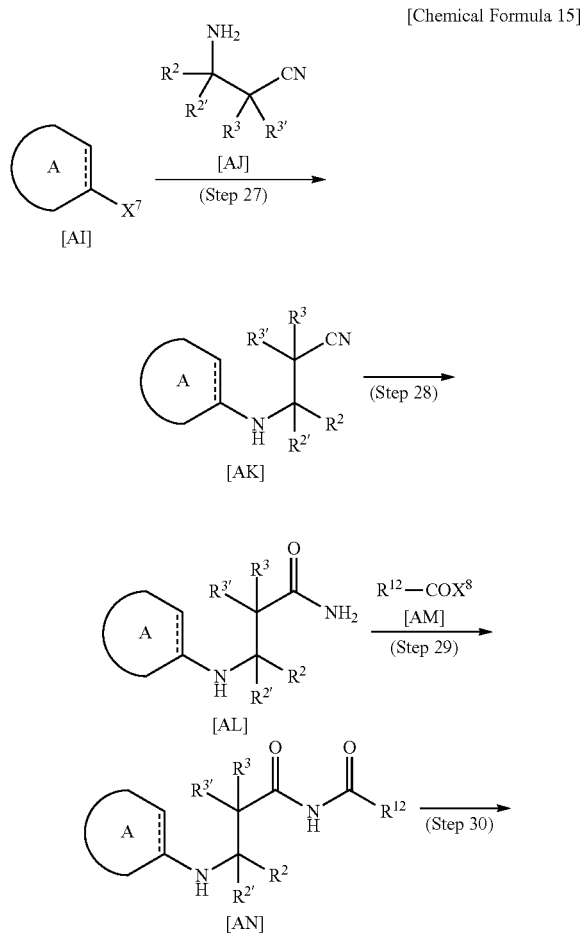

[Chemical Formula 15]

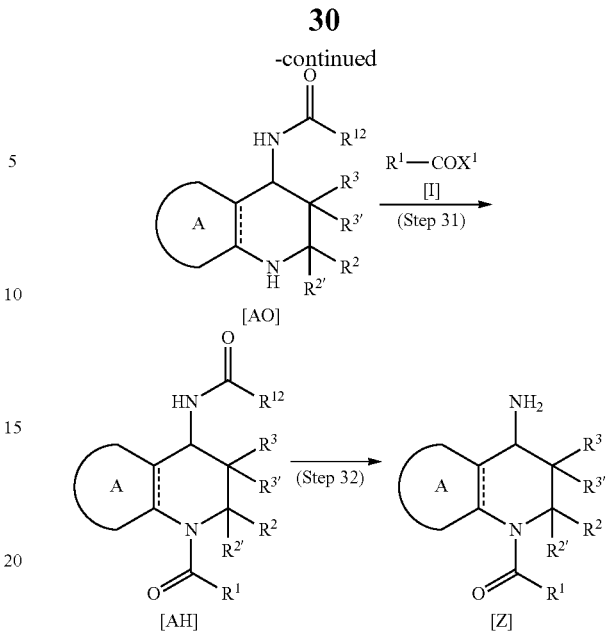

(wherein, $R^1$, $R^2$, $R^{2'}$, $R^3$, $R^{3'}$ and $R^{12}$ represent the same groups as previously defined, and $X^1$, $X^7$ and $X^8$ represent leaving groups).

(Step 27) Compound [AK] can be produced by reacting Compound [AI] and Compound [AJ] in a solvent in the presence or absence of a metal and in the presence of a base for 30 minutes to 40 hours (and preferably, 1 hour to 18 hours) while cooling or warming. Examples of the base include sodium tert-butoxide, pyridine, triethylamine, cesium carbonate, potassium carbonate, potassium phosphate, potassium tert-butoxide, lithium bis(trimethylsilyl) amide and 1,8-diazobicyclo[5.4.0]undec-7-ene. Examples of the metal include copper acetate, copper oxide, copper bromide, copper iodide, tris(dibenzylideneacetone) dipalladium, palladium acetate, bis(1,5-cyclooctadiene) nickel and palladium chloride. In addition, ligands such as (R)-(+)-2,2'-bis(diphenylphosphino)-1,1'-binaphthyl, (S)-(−)-2,2'-bis(diphenylphosphino)-1,1'-binaphthyl, (±)-2,2'-bis(biphenylphosphino)-1, 1'-binaphthyl, tris(o-tolyl)phosphine, 1,3-bis(diphenylphosphino)propane, tris(1-naphthyl)phosphine, tris (o-methoxyphenyl)phosphine, triphenylphosphine, 1,1'-bis (diphenylphosphino)ferrocene or o-(di-tert-butylphosphino) biphenyl are used suitably. Examples of the solvent include toluene, tetrahydrofuran, dioxane, dichloromethane, N,N-dimethylformamide and dimethoxyethane. These solvents may be used alone or in combination. Here, $X^7$ in Compound [AI] represents an atom or functional group that functions as a leaving group, and examples thereof include a halogen atom such as chlorine or bromine, and a boron-containing functional group such as a borono group.

(Step 28) Compound [AL] can be produced by reacting Compound [AK] in a solvent in the presence or absence of an acid for 30 minutes to 24 hours (and preferably, 1 hour to 4 hours) while cooling or warming. Examples of the acid include inorganic acids and organic acids. Examples of inorganic acids include hydrochloric acid, hydrobromic acid, sulfuric acid, phosphoric acid, tetrafluoroboric acid, perchloric acid and periodic acid. Examples of organic acids include sulfonic acids such as methanesulfonic acid, benzenesulfonic acid, p-toluenesulfonic acid or trifluoromethanesulfonic acid. Sulfuric acid is preferable. Examples of the solvent include aliphatic hydrocarbons such as pentane, hexane, heptane, octane, decane or cyclohexane, aromatic hydrocarbons such as benzene, toluene or xylene, halogenated hydrocarbons such as dichloromethane, 1,2-dichloroethane, chloroform, carbon tetrachloride or o-dichlorobenzene, and ethers such as diethyl ether, diisopropyl, ether, tert-butyl methyl ether, dimethoxyethane, ethylene glycol diethyl ether, tetrahydrofuran, 1,4-dioxane, 1,3-dioxolane or cyclopentyl methyl ether. These solvents can be used alone or in combination (and toluene is used preferably).

(Step 29) Compound [AN] can be produced by reacting Compound [AL] and Compound [AM] in a solvent and in the presence of a base for 5 minutes to 40 hours (and preferably, 1 hour to 18 hours) while cooling or warming. Examples of the base include lithium tert-butoxide, cesium carbonate, potassium carbonate, potassium phosphate, lithium bis(trimethylsilyl) amide, pyridine, triethanolamine and N,N-diisopropylethylamine. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination. Here, $X^8$ in Compound [AM] represents an atom or functional group that functions as a leaving group, and examples thereof include a halogen atom such as chlorine or bromine, and an acyl group such as a pivaloyl group.

(Step 30) Compound [AO] can be produced by reacting Compound [AN] in a solvent and allowing a reducing agent and acid to act thereon for 30 minutes to 40 hours (and preferably, for 1 hour to 6 hours) while cooling or warming. Examples of the reducing agent include sodium borohydride, sodium cyanoborohydride, sodium triacetoxyborohydride, zinc borohydride, borane, aluminum hydride and diisobutyl aluminum hydride. These reducing agents may be used alone or in combination. Examples of the acid include magnesium chloride, magnesium bromide, aluminum halides such as aluminum chloride or aluminum bromide, dialkyl aluminum halides such as diethyl aluminum chloride, diethyl aluminum bromide or diisopropyl aluminum chloride, trialkyl borates such as trimethyl borate, triethyl borate, tripropyl borate or tri-text-butyl borate, trialkoxy aluminum compounds such as triethoxyaluminum, triisopropoxyaluminum or tri-tert-butoxyaluminum, titanium halides such as titanium tetrachloride, tetraalkoxy titanium compounds such as tetraisopropoxytitanium, boron halides such as boron trifluoride, boron trichloride, boron tribromide or boron trifluoride-diethyl ether complex, and zinc halides such as zinc chloride or zinc bromide. Magnesium chloride is used preferably.

(Step 31) Compound [AH] can be produced by reacting Compound [AO] and Compound [I] in a solvent and in the presence or absence of a base for 5 minutes to 40 hours (and preferably 1 hour to 18 hours) while cooling or warming. Examples of the base include pyridine, triethylamine, N,N-diisopropylethylamine, N-methylmorpholine, N-methylpiperidine and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination. Here, $X^1$ in Compound [I] represents an atom or functional group that functions as a leaving group, and examples thereof include a halogen atom such as chlorine or bromine, and an acyl group such as a pivaloyl group.

(Step 32) Compound [Z] can be synthesized by reacting Compound [AH] in a solvent and in the presence of a reducing agent or the presence of an acid for 5 minutes to 40 hours (and preferably, 1 hour to 18 hours) while cooling or warming. A contact reduction reaction with hydrogen gas using a metal catalyst such a palladium carbon, palladium black, palladium hydroxide, platinum oxide or Rainey nickel is applied for the reduction method. Examples of the acid include inorganic acids such as hydrochloric acid, hydrobromic acid, sulfuric acid, phosphoric acid, tetrafluoroboric acid, perchloric acid or periodic acid. Examples of organic acids include formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, carboxylic acids such as glycolic acid, and sulfonic acids such as methanesulfonic acid, benzenesulfonic acid, p-toluenesulfonic acid or trifluoromethanesulfonic acid. Examples of Lewis acids include aluminum halides such as aluminum chloride or aluminum bromide, dialkyl aluminum halides such as diethyl aluminum chloride, diethyl aluminum bromide or diisopropyl aluminum chloride, trialkyl borates such as trimethyl borate, triethyl borate, tripropyl borate or tri-tert-butyl borate, trialkoxy aluminum compounds such as triethoxyaluminum, triisopropoxyaluminum or tri-tert-butoxyaluminum, titanium halides such as titanium tetrachloride, tetraalkoxy titanium compounds such as tetraisopropoxytitanium, boron halides such as boron trifluoride, boron trichloride, boron tribromide or boron trifluoride-diethyl ether complex, and zinc halides such as zinc chloride or zinc bromide. Hydrochloric acid, trifluoroacetic acid and trifluoromethanesulfonic acid are preferable.

An N-alkyl compound can be produced by using a known method such as alkylating Compound [Z] using a reductive amination reaction or alkylation reaction of an amino group, or by using an N-alkylated intermediate and a reagent.
1-9.

In addition, the 4-amino-fused piperidine compound [Z] used to produce Compound [D] in the present invention can also be produced by the following method with reference to a known procedure such as that described in WO 2005/100321:

[Chemical Formula 16]

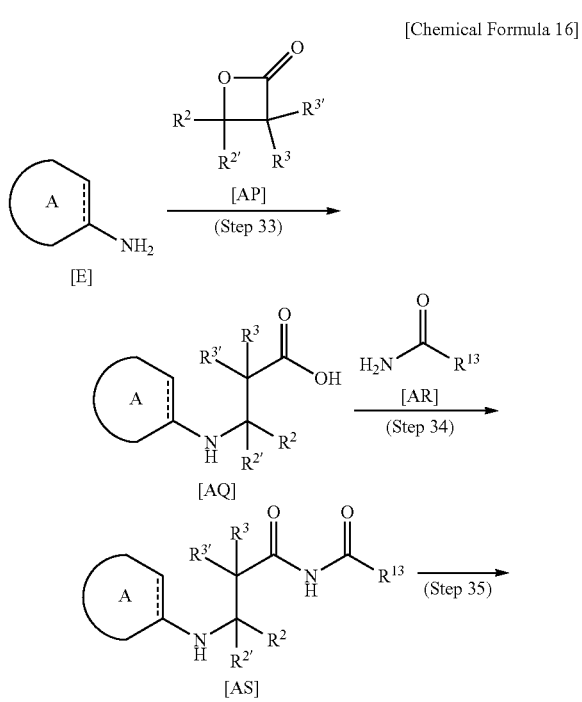

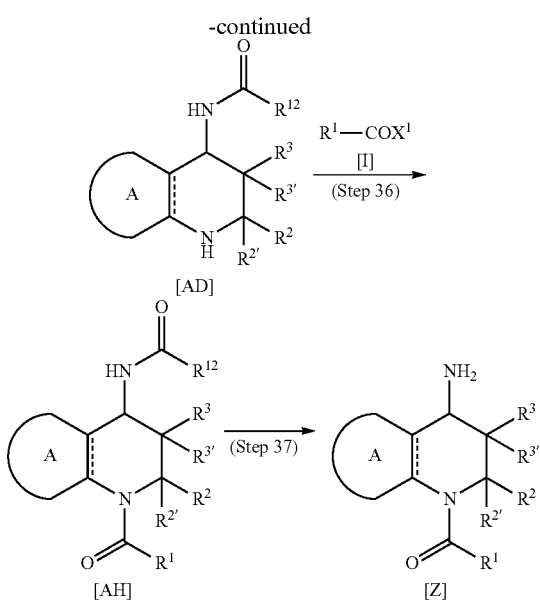

(wherein, $R^1$, $R^2$, $R^{2'}$, $R^3$, $R^{3'}$ and $R^{13}$ represent the same groups as previously defined, and $X^1$ represents a leaving group).

(Step 33) Compound [AQ] can be produced by reacting Compound [E] and Compound [AP] in a solvent for 5 minutes to 40 hours (and preferably 1 hour to 2 hours) while warming. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water. These solvents can be used alone or in combination.

(Step 34) Compound [AS] is obtained by reacting Compound [AQ] with an equal amount or excess of Compound [AR] in a solvent and in the presence or absence of a base for 5 minutes to 40 hours (and preferably 1 hour to 18 hours) while cooling or warming. At this time, examples of the reaction reagent that can be used include 1,1-carbonyldiimidazole (CDI), 1,3-dicyclohexylcarbodiimide (DCC), 1-ethyl-3-(3-dimethylaminopropyl)carbodiimide hydrochloride (WSC), oxalyl chloride and thionyl chloride. Examples of the base include organic bases such as pyridine, triethylamine or N,N-diisopropylethylamine, and inorganic bases such as potassium carbonate, sodium carbonate, potassium hydroxide, sodium hydroxide and lithium hydroxide. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination.

(Step 35) Compound [AD] can be produced by reacting Compound [AS] in a solvent by allowing a reducing agent and aid to act thereon for 30 minutes to 40 hours (and preferably, 1 hour to 6 hours) while cooling or warming. Examples of the reducing agent include sodium borohydride, sodium cyanoborohydride, sodium triacetoxyborohydride, zinc borohydride, borane, aluminum hydride and diisobutyl aluminum hydride. These reducing agents may be used alone or in combination. Examples of the acid include magnesium chloride, magnesium bromide, aluminum halides such as aluminum chloride or aluminum bromide, dialkyl aluminum halides such as diethyl aluminum chloride, diethyl aluminum bromide or diisopropyl aluminum chloride, trialkyl borates such as trimethyl borate, triethyl borate, tripropyl borate or tri-tert-butyl borate, trialkoxy aluminum compounds such as triethoxyaluminum, triisopropoxyaluminum or tri-tert-butoxyaluminum, titanium halides such as titanium tetrachloride, tetraalkoxy titanium compounds such as tetraisopropoxytitanium, boron halides such as boron trifluoride, boron trichloride, boron tribromide or boron trifluoride-diethyl ether complex, and zinc halides such as zinc chloride or zinc bromide. Magnesium chloride is used preferably.

(Step 36) Compound [AH] can be produced by reacting Compound [AD] and Compound [I] in a solvent and in the presence or absence of a base for 5 minutes to 40 hours (and preferably, 1 hour to 18 hours) while cooling or warming. Examples of the base include pyridine, triethylamine, N,N-diisopropylethylamine, N-methylmorpholine, N-methylpiperidine and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination. Here, $X^1$ in Compound [I] represents an atom or functional group that functions as a leaving group, and examples thereof include a halogen atom such as chlorine or bromine, and an acyl group such as a pivaloyl group.

(Step 37) Compound [Z] can be synthesized by reacting Compound [AH] in a solvent and in the presence of a reducing agent or the presence of an acid for 5 minutes to 40 hours (and preferably, 1 hour to 18 hours) while cooling or warming. A contact reduction reaction with hydrogen gas using a metal catalyst such a palladium carbon, palladium black, palladium hydroxide, platinum oxide or Rainey nickel is applied for the reduction method. Examples of the acid include inorganic acids such as hydrochloric acid, hydrobromic acid, sulfuric acid, phosphoric acid, tetrafluoroboric acid, perchloric acid or periodic acid. Examples of organic acids include formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, carboxylic acids such as glycolic acid, and sulfonic acids such as methanesulfonic acid, benzenesulfonic acid, p-toluenesulfonic acid or trifluoromethanesulfonic acid. Examples of Lewis acids include aluminum halides such as aluminum chloride or aluminum bromide, dialkyl aluminum halides such as diethyl aluminum chloride, diethyl aluminum bromide or diisopropyl aluminum chloride, trialkyl borates such as trimethyl borate, triethyl borate, tripropyl borate or tri-tert-butyl borate, trialkoxy aluminum compounds such as triethoxyaluminum, triisopropoxyaluminum or tri-test-butoxyaluminum, titanium halides such as titanium tetrachloride, tetraalkoxy titanium compounds such as tetraisopropoxytitanium, boron halides such as boron trifluoride, boron trichloride, boron tribromide or boron trifluoride-diethyl ether complex, and zinc halides such as zinc chloride or zinc bromide. Hydrochloric acid, trifluoroacetic acid and trifluoromethanesulfonic acid are preferable.

1-10.

The 4-amino-fused piperidine compound [Z] used to produce Compound [D] of the present invention can also be produced in accordance with the following production method with reference to a known procedure such as that described in WO 2002/53557.

[Chemical Formula 17]

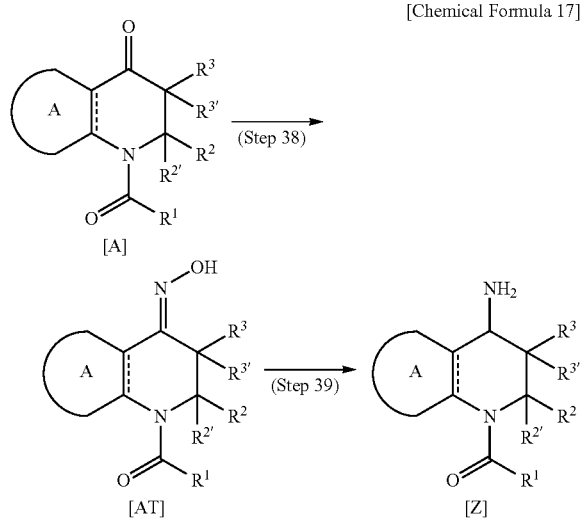

(Step 38) Compound [AT] can be produced by reacting Compound [A] with an hydroxylamine or hydroxylamine hydrochloride in a solvent and in the presence or absence of a base for 5 minutes to 40 hours (and preferably, 1 hour to 18 hours) while cooling or warming. Examples of the base include sodium acetate, sodium hydroxide, potassium hydroxide, lithium hydroxide, sodium carbonate, potassium carbonate and lithium bicarbonate. Examples of the solvent include organic solvents such as ethanol, methanol, isopropyl alcohol, dichloromethane, chloroform, toluene, diethyl ether, tetrahydrofuran, 1,4-dioxane, diisopropyl ether, dimethoxyethane, hexane, ethyl acetate, methyl-tert-butyl ether or N,N-dimethylformamide, and water, and these can be used alone or in combination.

(Step 39) Compound [Z] can be synthesized by reacting Compound [AT] in a solvent and in the presence of a reducing agent for 5 minutes to 40 hours (and preferably, 1 hour to 18 hours) while cooling or warming. Examples of the reduction method include contact reduction with hydrogen gas using a metal catalyst such as palladium carbon, palladium black, palladium hydroxide, platinum oxide or Rainey nickel, and a method using sodium borohydride, sodium cyanoborohydride, sodium triacetoxyborohydride, zinc borohyride, borane, aluminum hydride, diisobutyl aluminum hydride or sodium-alcohol. Examples of the solvent include organic solvents such as methanol, ethanol, isopropyl alcohol, dichloromethane, chloroform, toluene, N,N-dimethylformamide, methyl-tert-butyl ether, diethyl ether, 1,4-dioxane, tetrahydrofuran, acetic acid or ethyl acetate, and water, and these can be used alone or in combination.

In addition, the target compounds can also be produced by protecting substituents of each compound with suitable protecting groups, and then de-protecting the substituents following completion of the reaction step for the purpose of avoiding side reactions. Protecting and de-protecting substituents can be carried out by referring to typically used methods (such as that described in Protective Groups in Organic Synthesis, Third Edition, John Wiley & Sons, Inc. with respect to the conditions for protecting and de-protecting substituents.

Intermediates and target compounds obtained each of the aforementioned reactions can be isolated and purified as necessary by applying to purification methods commonly used in the field of synthetic organic chemistry, such as filtration, extraction, washing, drying, concentration, recrystallization or various types of chromatography. In addition, intermediates can be used in subsequent reactions without requiring any particular purification.

Moreover, various isomers can be isolated in accordance with ordinary methods by utilizing differences in physicochemical properties between the isomers. For example, racemic mixtures can be derived into optically pure isomers by optically resolving the racemic mixture by deriving into diastereomer salts with common optically active acids such as tartaric acid, or by using optically active column chromatography. In addition, mixtures of diastereomers can be separated by, for example, fractional crystallization or various types of chromatography. In addition, optically active compounds can also be produced by using suitably optically active raw materials.

The EPO production promoter, hemoglobin production promoter or anemia therapeutic agent of the present invention contains as an active ingredient thereof the fused piperidine compound represented by general formula (1), a salt thereof, or a solvate thereof, and can be used as a pharmaceutical composition. In that case, although the compound of the present invention may be used alone, it is normally used by incorporating a carrier and/or diluent that is acceptable for use in a pharmaceutical.

There are no particular limitations on the administration route, and can be suitably selected according to the treatment objective. For example, an oral preparation, injection preparation, suppository or inhalant may be used. Pharmaceutical compositions suitable for these administration forms can be produced by using known preparation methods.

In the case of preparing a solid preparation for oral administration, a tablet, coated tablet, granules, powder or capsule and the like can be produced using ordinary methods after having added a pharmaceutically acceptable vehicle, and as necessary, a binder, disintegration agent, lubricant, colorant, taste masking agent or odor masking agent and the like, to the compound represented by general formula (1). Additives typically used in the relevant technical field may be used as additives. Examples of vehicles include lactose, sucrose, sodium chloride, glucose, starch, calcium carbonate, kaolin, microcrystalline cellulose and silicic acid. Examples of binders include water, ethanol, propanol, simple syrup, liquid glucose, liquid starch, liquid gelatin, carboxymethyl cellulose, hydroxypropyl cellulose, hydroxypropyl starch, methyl cellulose, ethyl cellulose, shellac, calcium phosphate and polyvinylpyrrolidone. Examples of disintegration agents include dry starch, sodium alginate, powdered agar, sodium bicarbonate, calcium carbonate, sodium lauryl sulfate, monoglyceride stearate and lactose. Examples of lubricants include refined talc, stearates, borax and polyethylene glycol. Examples of taste masking agents include sucrose, orange peel, citric acid and tartaric acid.

In the case of preparing a liquid preparation for oral administration, a internally taken liquid preparation, syrup or elixir and the like can be produced using ordinary methods by adding a taste masking agent, buffer, stabilizer or odor masking agent and the like to the compound represented by general formula (1). Examples of taste making agents include those previously listed, examples of buffers include sodium citrate, and examples of stabilizers include tragacanth, gum arabic and gelatin.

In the case of preparing an injection preparation, a subcutaneous, intramuscular or intravenous injection preparation can be produced using ordinary methods by adding a pH adjuster, buffer, stabilizer, tonicity adjuster or local anesthetic and the like to the compound represented by general formula (1). Examples of pH adjusters and buffers include sodium citrate, sodium acetate and sodium phosphate. Examples of stabilizers include sodium pyrosulfite, EDTA, thioglycolic acid and thiolactic acid. Examples of local anesthetics include procaine hydrochloride and lidocaine hydrochloride. Examples of tonicity adjusters include sodium chloride and glucose.

In the case of preparing a suppository, a suppository can be produced using ordinary methods after having added a known suppository carrier, such as polyethylene glycol, lanolin, cacao butter or fatty acid triglyceride, and a surfactant (such as Tween (registered trademark)) as necessary, to the compound represented by general formula (1).

Other preferable preparations can also be suitably produced using ordinary methods in addition to those described above.

Although varying according to age, body weight, symptoms, administration form and number of administrations and the like, the normal adult dosage of the compound represented by general formula (1) of the present invention is preferably 1 mg to 1000 mg per day as the compound represented by general formula (1) administered once or divided among multiple administrations by oral administration or parenteral administration.

Although the following provides a more detailed explanation of the present invention through examples and test examples, the present invention is not limited to these examples.

EXAMPLES

Example 1

Production of cis-1-acetyl-4-[(4-chlorophenyl) amino]-2-methyl-3,4-dihydro-2H-[1,8]-naphthyridine (Compound 1)

[Step 1] 5.0 g of 2-chloronicotinic acid and 2.8 mL of thionyl chloride were dissolved in 60 mL of benzene and then refluxed while heating. Three hours later, after adding the reaction liquid to 50 mL of a separately prepared dichloromethane solution containing 4.6 g of N,O-dimethylhydroxyamine hydrochloride and 20 mL of pyridine while cooling with ice, the solution was stirred overnight at room temperature. Following completion of the reaction, the solution was concentrated under reduced pressure, and the resulting residue was purified by recrystallization (with a mixture of ethyl acetate and hexane) to obtain 5.1 g of 2-chloro-N-methoxy-N-methylnicotinamide in the form of pale yellow crystals (79%).

[Step 2] 3.0 g of the 2-chloro-N-methoxy-N-methylnicotinamide were dissolved in 30 mL of tetrahydrofuran, and 16.5 mL of 1.0 M allylmagnesium bromide/tetrahydrofuran solution were dropped in over the course of 30 minutes at −78° C. Following dropping, the solution was stirred for 1 hour at room temperature. Following completion of the reaction, the solution was acidified with 1N hydrochloric acid followed by neutralizing with a saturated aqueous solution of sodium bicarbonate and extracting three times with chloroform. After washing with saturated brine and dehydrating with anhydrous sodium sulfate, the solution was concentrated under reduced pressure to obtain 2.2 g of a mixture of 1-(2-chloropyridin-3-yl)but-2-en-1-one and 1-(2-chloropyridin-3-yl)but-3-en-1-one (81%).

[Step 3] 2.2 g of the mixture of 1-(2-chloropyridin-3-yl) but-2-en-1-one and 1-(2-chloropyridin-3-yl)but-3-en-1-one and 4-methoxybenzylamine were dissolved in 30 mL of ethanol and stirred overnight at 70° C. Following completion of the reaction, the solution was concentrated under reduced pressure and water was added to the resulting residue followed by extracting three times with chloroform. After washing with saturated brine and dehydrating with anhydrous sodium sulfate, the solution was concentrated under reduced pressure and the resulting residue was purified using silica gel chromatography (ethyl acetate:hexane=1:3) to obtain 2.7 g of 1-(4-methoxybenzyl)-4-oxo-2-methyl-2,3-dihydro-1H-[1, 8]-naphthyridine in the form of a yellow oil (80%).

[Step 4] 200 mg of the 1-(4-methoxybenzyl)-4-oxo-2-methyl-2,3-dihydro-1H-[1,8]-naphthyridine and 271 mg of 4-chloroaniline were dissolved in 4 ml of toluene followed by the addition of 0.35 mL of titanium tetrachloride (1.0 M dichloromethane solution) and refluxing while heating for 3 hours. Following completion of the reaction, the solution was filtered with celite followed by concentrating under reduced pressure to obtain 420 mg of a crude product.

[Step 5] 420 mg of the crude product and 89 mg of sodium cyanoborohydride were dissolved in 2 mL of methanol followed by adding one drop of acetic acid and stirring for 30 minutes at room temperature. Following completion of the reaction, the methanol was distilled off under reduced pressure. After neutralizing the resulting residue with a saturated aqueous solution of sodium bicarbonate, the solution was extracted three times with chloroform. After washing with saturated brine and dehydrating with anhydrous sodium sulfate, the solution was concentrated under reduced pressure and the resulting residue was purified using silica gel chromatography (ethyl acetate:hexane=1:3) to obtain 148 mg of 1-(4-methoxybenzyl)-4-[(4-chlorophenyl)amino]-2-methyl-3,4-dihydro-2H-[1,8]-naphthyridine in the form of a brown oil (53%, 2 steps).

[Step 6] 120 mg of the 1-(4-methoxybenzyl)-4-[(4-chlorophenyl)amino]-2-methyl-3,4-dihydro-2H-[1,8]-naphthyridine were dissolved in 3 mL of dichloromethane followed by the addition of 64 μL of trifluoroacetic acid anhydride and an excess of pyridine and stirring for 1 hour at room temperature. Following completion of the reaction, the reaction liquid was concentrated under reduced pressure and the resulting residue was purified using silica gel chromatography (ethyl acetate: hexane=1:5) to obtain 100 mg of N-(4-chlorophenyl)-2,2,2-trifluoro-N-[1-(4-methoxybenzyl-2-methyl-1,2,3,4-tetrahydro-1,8-naphthyridin-4-yl)acetoamide in the form of a pinkish white oil (67%).

[Step 7] 98 mg of the N-(4-chlorophenyl)-2,2,2-trifluoro-N-[1-(4-methoxybenzyl-2-methyl-1,2,3,4-tetrahydro-1,8-naphthyridin-4-yl)acetoamide were dissolved in 0.3 mL of dichloromethane and 0.3 mL of trifluoroacetic acid followed by stirring for 1.5 hours at room temperature. Following completion of the reaction, the solution was concentrated under reduced pressure and the resulting residue was neutralized with a saturated aqueous solution of sodium bicarbonate followed by extracting three times with chloroform. After washing with saturated brine and dehydrating with anhydrous sodium sulfate, the solution was concentrated under reduced pressure and the resulting residue was purified using silica gel chromatography (ethyl acetate:hexane=1:1) to obtain 78 mg of N-(4-chlorophenyl)-2,2,2-trifluoro-N-[2-methyl-1,2,3,4-tetrahydro-1,8-naphthyridin-4-yl]acetoamide in the form of a pale red oil (74%).

[Step 8] 70 mg of the N-(4-chlorophenyl)-2,2,2-trifluoro-N-[2-methyl-1,2,3,4-tetrahydro-1,8-naphthyridin-4-yl]acetoamide were dissolved in 0.3 mL of tetrahydrofuran followed by the addition of a 1.9 M sodium hexamethyldisilazane/tetrahydrofuran solution at −15° C. After stirring for 30 minutes at −15° C., 45 μL of acetic anhydride were added, and the solution was gradually returned to room temperature followed by stirring for 2 hours. Following completion of the reaction, the solution was neutralized with a saturated aqueous solution of ammonium chloride followed by extracting three times with ethyl acetate. After washing with saturated brine and dehydrating with anhydrous sodium sulfate, the solution was concentrated under reduced pressure and the resulting residue was purified using silica gel chromatography (ethyl acetate:hexane=2:1) to obtain 1.5 mg of the target compound in the form of a pale yellow oil (2.5%).

$^1$H-NMR (400 MHz, CDCl$_3$) δ: 1.25 (3H, d, J=6.3 Hz), 1.42 (1H, ddd, J=9.3, 12.0, 12.2 Hz), 2.33 (3H, s), 2.66 (1H, ddd, J=4.4, 8.3, 12.5 Hz), 3.86 (1H, d, J=6.8 Hz), 4.14-4.22 (1H, m), 4.78-4.92 (1H, m), 6.55 (2H, d, J=6.6 Hz), 7.08-7.17 (3H, m), 7.57 (1H, dd, J=1.0, 7.6 Hz), 8.35 (1H, dd, J=1.0, 5.0 Hz)

Example 2

Production of cis-1-acetyl-4-[(4-chlorophenyl)amino]-2-methyl-3,4-dihydro-2H-[1,6]-naphthyridine (Compound 2)

[Step 1] 200 mg of 4-chloropyridine were dissolved in 5 mL of diethyl ether followed by dropping in a 2 M solution of lithium diisopropylamide (LDA)/heptane, tetrahydrofuran and ethylbenzene over the course of 10 minutes at −78° C. After stirring for 1 hour at −78° C., 2 ml of a separately prepared diethyl ether solution containing 489 mg of tert-butyl-2-methyl-4-oxoazetidine-1-carboxylate were added followed by slowly returning to room temperature and stirring overnight. Following completion of the reaction, water was added followed by extracting three times with ethyl acetate. After washing with saturated brine and dehydrating with anhydrous sodium sulfate, the solution was concentrated under reduced pressure and the resulting residue was purified using silica gel chromatography (ethyl acetate:hexane=1:2) to obtain 275 mg of tert-butyl-4-(4-chloropyridin-3-yl)-4-oxobutan-2-yl carbamate in the form of a pale yellow oil (52%).

[Step 2] 62 mg of the tert-butyl-4-(4-chloropyridin-3-yl)-4-oxobutan-2-yl carbamate were dissolved in 2 mL of ethyl acetate followed by adding 1 mL of 4 N hydrochloric acid/ethyl acetate while cooling with ice and stirring for 5 hours at room temperature. Following completion of the reaction, the solution was concentrated under reduced pressure and the resulting residue was washed three times with ethyl acetate to obtain 64 mg of a crude product of 3-amino-1-(4-chloropyridin-3-yl)butan-1-one dihydrochloride.

[Step 3] 64 mg of the crude product of 3-amino-1-(4-chloropyridin-3-yl)butan-1-one dihydrochloride were dissolved in 2 mL of N-dimethylformamide followed by adding 0.18 mL of diisopropylethylamine while cooling with ice and stirring for 1 hour at room temperature. This was followed by additionally stirring overnight at 100° C. Following completion of the reaction, water was added followed by extracting three times with chloroform. After washing with saturated brine and dehydrating with anhydrous sodium sulfate, the solution was concentrated under reduced pressure and the resulting residue was purified using silica gel chromatography (methanol:chloroform=1:10) to obtain 9 mg of 4-oxo-2-methyl-2,3-dihydro-1H-[1,6]naphthyridine in the form of a pale yellow oil (27%).

[Step 4] 30 mg of the 4-oxo-2-methyl-2,3-dihydro-1H-[1,6]naphthyridine were dissolved in 2 mL of dichloromethane followed by adding 0.1 mL of triethylamine and 35 μL of acetic anhydride and stirring overnight at 40° C. Following completion of the reaction, the solution was concentrated under reduced pressure and the resulting residue was purified using silica gel chromatography (ethyl acetate) to obtain 7 mg of 1-acetyl-4-oxo-2-methyl-2,3-dihydro-1H-[1,6]naphthyridine in the form of a pale yellow oil (18%).

[Step 5] 9 mg of the 1-acetyl-4-oxo-2-methyl-2,3-dihydro-1H-[1,6]naphthyridine and 11 mg of 4-chloroaniline were dissolved in 0.1 mL of toluene followed by adding 44 μL of titanium tetrachloride (1.0 M dichloromethane solution) while cooling with ice and refluxing while heating overnight. Following completion of the reaction, the solution was filtered with celite and concentrated under reduced pressure to obtain 20 mg of a crude product.

[Step 6] 20 mg of the crude product and 14 mg of sodium cyanoborohydride were dissolved in 2 mL of methanol followed by adding one drop of acetic acid and stirring for 1.5 hours at room temperature. Following completion of the reaction, the methanol was distilled off under reduced pressure. The resulting residue was neutralized with saturated sodium bicarbonate and then extracted three times with chloroform. The resulting residue was purified using silica gel chromatography (ethyl acetate:hexane=5:1) to obtain 1.1 mg of the target compound in the form of a pale yellow oil (8%, 2 steps).

$^1$H-NMR (400 MHz, CDCl$_3$) δ: 1.23 (3H, d, J=6.4 Hz), 1.44-1.53 (1H, m), 2.27 (3H, s), 2.66 (1H, ddd, J=4.4, 8.2 16.7 Hz), 3.83 (1H, d, J=7.8 Hz), 4.24-4.31 (1H, m), 4.75-3.81 (1H, m), 6.59 (2H, d, J=6.6 Hz), 7.13-7.18 (3H, m), 8.50 (1H, s), 8.54 (1H, d, J=5.4 Hz)

Example 3

Production of cis-1-acetyl-4-[(4-chlorophenyl)amino]-2-methyl-3,4-dihydro-2H-[1,5]-naphthyridine (Compound 3)

[Step 1] 500 mg of 3-amino-6-bromopyridine were dissolved in 12 mL of dichloromethane followed by adding 616 mg of anhydrous sodium sulfate, adding 0.18 mL of acetoaldehyde at −20° C., and stirring for 2 hours. After filtering the reaction liquid and removing the sodium sulfate, 563 mg of benzyl vinyl carbamate were added. Trifluoroborane etherate was then dropped into the reaction liquid at −20° C. over the course of 15 minutes followed by stirring for 3 hours at −10° C. or lower. Following completion of the reaction, the solution was neutralized with saturated sodium bicarbonate followed by extracting three times with chloroform. After washing with saturated brine and dehydrating with anhydrous sodium sulfate, the solution was concentrated under reduced pressure and the resulting residue was purified using silica gel chromatography (ethyl acetate:hexane=1:2) to obtain 821 mg of benzyl-6-bromo-2-methyl-1,2,3,4-tetrahydro-1,5-naphthyridin-4-yl carbamate in the form of a pale yellow amorphous substance (76%).

[Step 2] 479 mg of the benzyl-6-bromo-2-methyl-1,2,3,4-tetrahydro-1,5-naphthyridin-4-yl carbamate were dissolved in 5 mL of dichloromethane followed by adding 0.31 mL of pyridine. 0.14 mL of acetyl chloride were then added while cooling with ice followed by stirring for 30 minutes at room temperature. Following completion of the reaction, the solution was neutralized with saturated aqueous sodium bicarbonate solution followed by extracting three times with chloroform. After washing with saturated brine and dehydrating with anhydrous sodium sulfate, the solution was concentrated under reduced pressure and the resulting residue was purified using silica gel chromatography (ethyl acetate:hexane=1:1) to obtain 376 mg of benzyl-1-acetyl-6-bromo-2-methyl-1,2, 3,4-tetrahydro-1,5-naphthyridin-4-yl carbamate in the form of a pale yellow amorphous substance (71%).

[Step 3] 279 mg of the benzyl-1-acetyl-6-bromo-2-methyl-1,2,3,4-tetrahydro-1,5-naphthyridin-4-yl carbamate and 126 mg of ammonium formate were dissolved in 5 mL of ethanol followed by adding 112 mg of 10% palladium carbon and stirring for 6 hours under normal pressure in a hydrogen atmosphere at room temperature. Following completion of the reaction, the solution was filtered with celite and concentrated under reduced pressure. The resulting residue was neutralized with saturated sodium bicarbonate and extracted five times with chloroform. After washing with saturated brine and dehydrating with anhydrous sodium sulfate, the solution was concentrated under reduced pressure and the resulting residue was purified using silica gel chromatography (saturated ammonia/methanol:chloroform=1:10) to obtain 85 mg of 1-acetyl-4-amino-2-methyl-3,4-dihydro-2H-[1,5]naphthyridine in the form of a red solid (62%).

[Step 4] 15 mg of the 1-acetyl-4-amino-2-methyl-3,4-dihydro-2H-[1,5] naphthyridine and 23 mg of 4-chlorophenylboronic acid were dissolved in 0.3 mL of DMF followed by adding 27 mg of divalent capper acetate and 18 μL of pyridine and stirring for 5 hours at room temperature in the presence of air. Following completion of the reaction, the solution was filtered with celite followed by the addition of water and extracting three times with ethyl acetate. After washing with saturated brine and dehydrating with anhydrous sodium sulfate, the solution was concentrated under reduced pressure and the resulting residue was purified using silica gel chromatography (ethyl acetate:hexane=1:1) to obtain 13 mg of the target compound in the form of a pale yellow solid (57%).

$^1$H-NMR (400 MHz, CDCl$_3$) δ: 1.09-1.28 (4H, m), 2.17 (3H, s), 2.97 (1H, ddd, J=4.2, 8.3, 12.9 Hz), 4.29 (1H, dd, J=3.9, 12.0 Hz), 4.76-4.84 (1H, m), 5.70-5.78 (1H, br), 6.69 (2H, d, J=8.8 Hz), 7.18 (1H, d, J=8.8 Hz), 7.31 (1H, dd, J=4.8, 7.9 Hz), 7.50-7.62 (1H, br), 8.43 (1H, d, J=4.8 Hz)

Example 4

Production of 1-(7-(4-chlorophenylamino)-5-methyl-6,7-dihydrothieno[3,2-b]pyridine-4(5H)-yl)ethanone (Compound 4)

[Step 1] 652 mg (2.9 mmol) of ethyl 7-hydroxythieno[3,2-b]pyridine-6-carboxylate (Reference Document: WO 2005/97806) were dissolved in anhydrous dichloroethane followed by adding 0.7 mL (8.8 mmol) of anhydrous pyridine and 1.9 g (8.8 mmol) of di-tert-butyl dicarbonate and stirring for 18 hours at room temperature. Following completion of the reaction, water was added to the reaction liquid followed by extraction with chloroform. After dehydrating the organic layer with anhydrous sodium sulfate, the organic layer was concentrated under reduced pressure and the resulting residue was purified using Silica gel chromatography (chloroform:methanol=30:1) to obtain 732 mg of 4-tert-butyl-6-ethyl-7-oxothieno[3,2-b]pyridine-4,6(7H)-dicarboxylate in the form of a pale brown solid (78%).

$^1$H-NMR (270 MHz, CDCl$_3$) δ: 1.42 (3H, t, J=7.1 Hz), 1.71 (9H, s), 4.41 (2H, q, J=7.0 Hz), 7.73 (1H, d, J=5.6 Hz), 7.99 (1H, d, J=5.6 Hz), 9.09 (1H, s)

[Step 2] A tetrahydrofuran mixed solution (30 mL) of 438 mg (1.4 mmol) of the 4-tert-butyl-6-ethyl-7-oxothieno[3,2-b]pyridine-4,6(7H)-dicarboxylate and 516 mg (2.7 mmol) of copper iodide was stirred in an argon atmosphere at −78° C. followed by dropping in 2.8 mL (2.7 mmol) of a tetrahydrofuran solution of methylmagnesium bromide (0.97 mol/L). The solution was gradually returned to room temperature by stirring over the course of 18 hours. Following completion of the reaction, a saturated aqueous ammonium chloride solution was added to the reaction liquid and extracted with chloroform. The organic layer was washed with saturated aqueous ammonium chloride solution and further washed with saturated brine. After dehydrating with anhydrous sodium sulfate, the solution was concentrated under reduced pressure to obtain 360 mg of 4-text-butyl-6-ethyl-5-methyl-7-oxo-6,7-dihydrothieno[3,2-b]pyridine-4,6(5H)-dicarboxylate in the form of a yellowish brown oil (79%).

$^1$H-NMR (400 MHz, CDCl$_3$) δ: 1.20 (3H, t, J=7.2 Hz), 1.33 (3H, d, J=6.8 Hz), 1.58 (9H, s), 3.31 (1H, d, J=1.7 Hz), 4.12-4.18 (2H, m), 5.30-5.37 (1H, m), 7.58-7.67 (2H, m)

[Step 3] 331 mg (0.98 mmol) of the 4-tert-butyl-6-ethyl-5-methyl-7-oxo-6,7-dihydrothieno[3,2-b]pyridine-4,6(5H)-dicarboxylate were suspended in 10 mL of ethanol followed by the addition of 5 mL (10 mmol) of aqueous sodium hydroxide solution (2 mol/L) to obtain a red solution. The solution was stirred for 4 hours while refluxing in an oil bath at 100° C. Following completion of the reaction, water was added to the reaction liquid followed by extraction with chloroform. The organic layer was dehydrated with anhydrous sodium sulfate and then concentrated under reduced pressure to obtain 123 mg of 5-methyl-5,6-dihydrothieno[3,2-b]pyridin-7(4H)-one in the form of a pale brown solid (75%).

$^1$H-NMR (400 MHz, CDCl$_3$) δ: 1.36 (3H, d, J=6.3 Hz), 2.40-2.58 (2H, m), 3.85-3.92 (1H, m), 4.65 (1H, brs), 6.53 (1H, d, J=5.4 Hz), 7.51 (1H, d, J=5.4 Hz)

[Step 4] 123 mg (0.74 mmol) of the 5-methyl-5,6-dihydrothieno[3,2-b]pyridin-7(4H)-one were dissolved in 4 mL of anhydrous dichloromethane followed by sequentially adding 0.12 mL (1.5 mmol) of anhydrous pyridine and 0.078 mL (1.1 mmol) of acetyl chloride and stirring for 1 hour at room temperature. Following completion of the reaction, ethanol was added, the solution was concentrated under reduced pressure and then additionally boiled with toluene. The residue was purified by silica gel column chromatography (n-hexane:ethyl acetate=1:1) to obtain 111 mg of 4-acetyl-5-methyl-5,6-dihydrothieno[3,2-b]pyridin-7(4H)-one in the form of a pale brown oil (72%).

$^1$H-NMR (270 MHz, CDCl$_3$) δ: 1.34 (3H, d, J=6.9 Hz), 2.41 (3H, s), 2.56 (1H, dd, J=17.0, 1.8 Hz), 3.07 (1H, dd, J=17.1, 5.6 Hz), 4.76-5.00 (1H, m), 7.66-7.69 (2H, m)

[Step 5] 0.16 mL (0.16 mmol) of a dichloromethane solution of titanium tetrachloride (1 mol/L) were dropped in an argon atmosphere into an anhydrous toluene solution (1 mL) containing 34 mg (0.16 mmol) of the 4-acetyl-5-methyl-5,6-dihydrothieno[3,2-b]pyridin-7(4H)-one and 42 mg (0.33 mmol) of 4-chloroaniline followed by stirring for 1 hour while refluxing in an oil bath at 130° C. Following completion of the reaction, the solution was allowed to cool on standing to room temperature followed by the addition of 2 mL of diethyl ether and removal of the solid by filtering with celite. The filtrate was then concentrated under reduced pressure to obtain 19 mg of a mixture containing an intermediate imine in the form of a yellow solid. The resulting solid was dissolved in 1 ml of methanol followed by the sequential addition of 20 mg (0.32 mmol) of sodium cyanoborohydride and 19 mg (0.32 mmol) of acetic acid and stirring for 1 hour at room temperature. Following completion of the reaction, water was added followed by extraction with chloroform. The organic layer was dehydrated with anhydrous sodium sulfate and concentrated under reduced pressure. The resulting residue was purified by silica gel column chromatography (n-hexane:ethyl acetate=1:1) to obtain 4.2 mg of cis-1-(7-(4-chlorophenylamino)-5-methyl-6,7-dihydrothieno[3,2-b]pyridin-4 (5H)-yl)ethanone (8%) in the form of a yellowish-brown oil, and 1.0 mg of trans-1-(7-(4-chlorophenylamino)-5-methyl-6,7-dihydrothieno[3,2-b]pyridin-4(5H)-yl)ethanone in the form of a white solid (2%).

cis-1-(7-(4-chlorophenylamino)-5-methyl-6,7-dihydrothieno[3,2-b]pyridin-4(5H)-yl)ethanone $^1$H-NMR (270 MHz, CDCl$_3$) δ: 1.22 (3H, d, J=8.4 Hz), 2.30 (3H, s), 2.79-2.90 (2H, m), 4.21-4.44 (1H, m), 4.67-4.73 (1H, m), 6.55-6.62 (2H, m), 7.08 (1H, d, J=4.9 Hz), 7.14-7.21 (2H, m), 7.23-7.27 (1H, m)

trans-1-(7-(4-chlorophenylamino)-5-methyl-6,7-dihydrothieno[3,2-b]pyridin-4(5H)-yl)ethanone $^1$H-NMR (270 MHz, CDCl$_3$) δ: 1.31 (3H, d, J=6.6 Hz), 1.78-1.92 (1H, m), 2.31 (3H, s), 2.36-2.49 (1H, m), 3.67-3.92 (1H, m), 4.76-4.95 (1H, m), 6.61-6.68 (2H, m), 7.13-7.20 (3H, m), 7.25-7.27 (1H, m)

Example 5

Production of cis-1-acetyl-4-[(4-chlorophenyl)amino]-2-methyl-1,2,3,4-tetrahydro-benzo[h]quinoline (Compound 5)

[Step 1] 2.0 g of 1-naphthylamine and 2.6 g of 1H-benzotriazole were dissolved in 80 mL of toluene followed by adding 10 mL of a toluene solution containing 1.4 mL of acetoaldehyde and stirring overnight at room temperature. Following completion of the reaction, 30 mL of heptane were added and stirred for 1 hour followed by filtering to obtain 3.8 g of a crude product of N-[1-(1H-benzo[d][1,2,3]triazol-1-yl)ethyl]naphthalene-1-amine.

[Step 2] 300 mg of the N-[1-(1H-benzo[d][1,2,3]triazol-1-yl)ethyl]naphthalene-1-amine and 184 mg of benzyl vinyl carbamate were dissolved in 3.5 mL of toluene followed by adding 2 mg of p-toluenesulfonic acid monohydrate and stirring for 30 minutes while heating at 70° C. Following completion of the reaction, the solution was neutralized by adding saturated aqueous sodium bicarbonate solution followed by extracting three times with chloroform. After washing with saturated brine and dehydrating with anhydrous sodium sulfate, the solution was concentrated under reduced pressure and the resulting residue was purified using silica gel chromatography (ethyl acetate:hexane 1:5) to obtain 200 mg of cis-benzyl 2-methyl-1,2,3,4-tetrahydrobenzo[h]quinolin-4-yl carbamate in the form of a white solid (53%).

[Step 3] 200 mg of the cis-benzyl 2-methyl-1,2,3,4-tetrahydrobenzo[h]quinolin-4-yl carbamate and 0.13 mL of pyridine were dissolved in 5 mL of dichloromethane followed by adding 59 μL of acetyl chloride while cooling with ice and stirring for 3 hours at room temperature. Following completion of the reaction, the solution was concentrated under reduced pressure and saturated aqueous sodium bicarbonate solution was added to the resulting residue followed by extracting three times with chloroform. After washing with saturated brine and dehydrating with anhydrous sodium sulfate, the solution was concentrated under reduced pressure and the resulting residue was purified using silica gel chromatography (ethyl acetate:hexane=1:2) to obtain 213 mg of cis-benzyl 1-acetyl-2-methyl-1,2,3,4-tetrahydrobenzo[h]quinolin-4-yl carbamate in the form of a white amorphous substance (100%).

[Step 4] 214 mg of the cis-benzyl 1-acetyl-2-methyl-1,2,3,4-tetrahydrobenzo[h]quinolin-4-yl carbamate and 104 mg of ammonium formate were dissolved in 5 ml of ethanol followed by the addition of 64 mg of 10% palladium carbon and stirring for 6 hours at normal pressure in a hydrogen atmosphere at room temperature. Following completion of the reaction, the solution was filtered with celite and concentrated under reduced pressure. The resulting residue was neutralized with saturated aqueous sodium bicarbonate solution followed by extracting three times with chloroform. After washing with saturated brine and dehydrating with anhydrous sodium sulfate, the solution was concentrated under reduced pressure to obtain 135 mg of cis-1-acetyl-4-amino-2-methyl-1,2,3,4-tetrahydrobenzo[h]quinoline in the form of a colorless oil (96%).

[Step 5] 91 mg of the cis-1-acetyl-4-amino-2-methyl-1,2,3,4-tetrahydrobenzo[h]quinoline and 84 mg of 4-chlorophenylboronic acid were dissolved in 2.5 mL of DMF followed by adding 130 mg of divalent copper acetate and 87 μL of pyridine and stirring for 30 minutes at room temperature in the presence of air. Following completion of the reaction, the solution was filtered with celite followed by the addition of water and extracting three times with ethyl acetate. After washing with saturated brine and dehydrating with anhydrous sodium sulfate, the solution was concentrated under reduced pressure and the resulting residue was purified using silica gel chromatography (ethyl acetate:hexane=1:1) to obtain 25 mg of the target compound in the form of a yellow solid (19%).

$^1$H-NMR (400 MHz, CDCl$_3$) δ: 1.12 (3H, d, J=6.6 Hz), 1.20-1.30 (1H, m), 1.87 (3H, s), 2.77 (1H, ddd, J=4.6, 8.1, 12.7 Hz), 3.97 (1H, d, J=6.6 Hz), 4.20-4.29 (1H, m), 5.24-5.36 (1H, m), 6.59 (2H, d, J=6.6 Hz), 7.16 (2H, d, J=6.6 Hz), 7.35-7.65 (3H, m), 7.67-7.85 (3H, m)

Example 6

Production of cis-1-[(1-(4-chlorophenylamino)-3-methyl-2,3-dihydro-4,7-phenanthrolin-4(1H)-yl]ethanone (Compound 6)

[Step 1] 5 mL of a toluene suspension of 1.0 mg (3.5 mmol) of 6-aminoquinoline were added to 5 mL of a toluene suspension of 826 mg (3.5 mmol) of benzotriazole and stirred. 5 mL of a toluene solution containing 0.22 mL (3.8 mmol) of acetoaldehyde were dropped therein followed by stirring for 18 hours at room temperature. Following completion of the reaction, 15 mL of n-hexane were added followed by filtering out the solid. The solid was washed with n-hexane and dried under reduced pressure to obtain 20 g of N-[1-(1H-benzo[d][1,2,3]triazol-1-yl)ethyl]quinolin-6-amine in the form of a white solid (99%).

[Step 2] 292 mg (1.0 mmol) of the N-[1-(1H-benzo[d][1,2,3]triazol-1-yl)ethyl]quinolin-6-amine, 179 mg (1.0 mmol) of benzyl vinyl carbamate and 2 mg (0.01 mmol) of p-toluenesulfonic acid were suspended in 5 mL of toluene and stirred for 5 hours at 70° C. (which gradually became a homogeneous system that became a yellow solution 1 hour later). Following completion of the reaction, the reaction liquid was washed with a saturated aqueous sodium bicarbonate solution, the washing was extracted with ethyl acetate, and the organic layers were combined and washed with saturated brine. The solution was then dehydrated with anhydrous sodium sulfate, concentrated under reduced pressure, and the resulting residue was purified by silica gel column chromatography (chloroform:methanol=20:1) to obtain 209 mg of a crude form of benzyl 3-methyl-1,2,3,4-tetrahydro-4,7-phenanthrolin-1-yl carbamate in the form of a pale yellow foam-like substance.

[Step 3] 207 mg (approx. 0.60 mmol) of the benzyl 3-methyl-1,2,3,4-tetrahydro-4,7-phenanthrolin-1-yl carbamate were dissolved in 4 mL of dichloromethane followed by adding 94 mg (1.2 mmol) of pyridine. 70 mg of acetyl chloride were further added and stirred for 1 hour at room temperature. Following completion of the reaction, aqueous hydrochloric acid (1 mol/L) was added followed by extraction with chloroform. The organic layer was washed with water and then dehydrated with anhydrous sodium sulfate. The solution was then concentrated under reduced pressure and the resulting residue was purified by silica gel column chromatography (ethyl acetate) to obtain 67 mg of benzyl 4-acetyl-3-methyl-1,2,3,4-tetrahydro-4,7-phenanthrolin-1-yl carbamate in the form of a white amorphous substance (17%, 2 steps).

$^1$H-NMR (270 MHz, CDCl$_3$) δ: 1.20-1.27 (1H, m), 1.31 (3H, d, J=6.9 Hz), 2.30 (3H, s), 2.31-2.40 (2H, m), 4.96 (1H, d, J=8.9 Hz), 5.18 (3H, dd, J=35.6, 12.2 Hz), 5.42-5.53 (1H, m), 7.29-7.41 (6H, m), 7.71 (1H, brs), 8.00 (1H, d, J=9.2 Hz), 8.20 (1H, d, J=7.9 Hz), 8.86 (1H, dd, J=4.5, 1.5 Hz)

[Step 4] 65 mg (0.17 mmol) of the benzyl 4-acetyl-3-methyl-1,2,3,4-tetrahydro-4,7-phenanthrolin-1-yl carbamate were dissolved in 2 mL of ethanol followed by adding 42 mg (0.67 mmol) of ammonium formate and further adding 30 mg of palladium carbon. The system was then replaced with hydrogen and stirred for 1 hour. Following completion of the reaction, the reaction liquid was filtered with celite and the filtrate was concentrated under reduced pressure. The residue was dissolved in chloroform, washed with saturated aqueous sodium bicarbonate solution, and dehydrated with anhydrous sodium sulfate. The solution was concentrated under reduced pressure to obtain 37 mg of 1-(1-amino-3-methyl-2,3-dihydro-4,7-phenanthrolin-4(1H)-yl)ethanone in the form of a yellowish-brown oil (85%).

$^1$H-NMR (270 MHz, CDCl$_3$) δ: 1.40 (3H, d, J=6.9 Hz), 2.06 (1H, d, J=13.5 Hz), 2.27 (3H, s), 2.45 (1H, dt, J=14.3, 5.7 Hz), 4.63 (1H, d, J=4.9 Hz), 7.45, (1H, dd, J=8.6, 4.3 Hz), 7.65 (1H, brs), 7.98 (1H, d, J=9.2 Hz), 8.65 (1H, d, J=9.2 Hz), 8.87 (1H, dd, J=4.3, 1.6 Hz)

[Step 5] 36 mg (0.14 mmol) of the 1-(1-amino-3-methyl-2,3-dihydro-4,7-phenanthrolin-4(1H)-yl)ethanone, 51 mg (0.28 mmol) of copper (II) acetate, 43 mg (0.42 mmol) of triethylamine and 2 ml of a dichloromethane suspension containing 27 mg of molecular sieve (4A) were vigorously stirred for 18 hours. Following completion of the reaction, aqueous ammonium chloride solution was added followed by extraction with chloroform. The extract was washed with water and the organic layer was dehydrated with anhydrous sodium sulfate. The residue obtained by concentrating under reduced pressure was purified by silica gel column chromatography (ethyl acetate) and NH silica gel column chromatography (n-hexane:ethyl acetate=2:1) followed by crystallizing with diethyl ether and n-hexane to obtain 7 mg of the target compound in the form of a pale yellow crystalline powder (13%).

$^1$H-NMR (270 MHz, CDCl$_3$) δ: 1.35 (3H, d, J=6.9 Hz), 2.21-2.45 (5H, m), 3.76 (1H, d, J=6.9 Hz), 4.98-5.07 (2H, m), 6.57-6.61 (2H, m), 7.20-7.25 (2H, m), 7.34 (1H, dd, J=8.6, 4.3 Hz), 7.78 (1H, brs), 8.03 (1H, d, J=9.2 Hz), 8.11 (1H, d, J=8.6 Hz), 8.83-8.87 (1H, m)

Example 7

Production of cis-6-acetyl-9-(4-chlorophenylamino)-7-methyl-6,7,8,9-tetrahydro-3H-pyrrolo[3,2-f]quinoline (Compound 7)

[Step 1] N-[1-(1H-benzo[d][1,2,3]triazol-1-yl)ethyl]-1-tosyl-1H-indol-5-amine was obtained in the form of a crude product in the same manner as Step 1 of Example 5 by using 1-tosyl-1H-indol-5-amine as raw material. This crude product was then processed in the same manner as Step 2 of Example 5 to obtain 200 mg of benzyl 7-methyl-3-tosyl-6,7,8,9-tetrahydro-3H-pyrrolo[3,2-f]quinolin-9-yl carbamate in the form of a pale yellow amorphous substance (39.0%).

$^1$H-NMR (400 MHz, CDCl$_5$) δ: 1.20 (3H, d, J=6.1 Hz), 1.54-1.61 (1H, m), 2.34 (1H, s), 2.42-2.50 (1H, m), 3.34-3.46 (1H, m), 4.86 (1H, d, J=9.0 Hz), 5.12-5.28 (3H, m), 6.49 (1H, d, J=3.7 Hz), 6.52 (1H, d, J=8.8 Hz), 7.20 (2H, d, J=8.6 Hz), 7.32-7.40 (6H, m), 7.69 (1H, d, J=8.8 Hz), 7.70 (1H, d, J=8.3 Hz)

[Step 2] Benzyl 7-acetyl-7-methyl-3-tosyl-6,7,8,9-tetrahydro-3H-pyrrolo[3,2-f]quinolin-9-yl carbamate was processed in the same manner as Step 3 of Example 5 to obtain benzyl 6-acetyl-7-methyl-3-tosyl-6,7,8,9-tetrahydro-3H-pyrrolo[3,2-f]quinolin-9-yl carbamate in the form of a crude product. This crude product was processed in the same manner as Step 4 of Example 5 to obtain 138 mg of 6-acetyl-9-amino-7-methyl-3-tosyl-6,7,8,9-tetrahydro-3H-pyrrolo[3,2-f]quinoline in the form of a yellow oil (85.2%).

$^1$H-NMR (400 MHz, CDCl$_3$) δ: 1.11 (3H, d, J=5.8 Hz), 1.30-1.47 (1H, br), 2.05 (3H, s), 2.37 (3H, s), 2.45 (1H, ddd, J=12.9, 7.9, 4.9 Hz), 4.02-4.12 (1H, m), 4.94 (1H, br), 7.06 (1H, br), 7.26 (2H, d, J8.8 Hz), 7.32 (1H, br), 7.61 (1H, d, J=3.6 Hz), 7.79 (2H, d, J=8.3 Hz), 7.88 (1H, d, J=8.8 Hz)

[Step 3] 30.4 mg of 6-acetyl-9-(4-chlorophenylamino)-7-methyl-3-tosyl-6,7,8,9-tetrahydro-3H-pyrrolo[3,2-f]quinoline as obtained in the form of a yellow oil in the same manner as Step 5 of Example 5 by using the 6-acetyl-9-amino-7-methyl-3-tosyl-6,7,8,9-tetrahydro-3H-pyrrolo[3,2-f]quinoline as raw material (19.4%).

$^1$H-NMR (400 MHz, CDCl$_3$) δ: 1.09-1.20 (4H, m), 2.17 (3H, s), 2.38 (3H, s), 2.44-2.54 (1H, m), 3.85 (1H, d, J=6.6 Hz), 4.40-4.52 (1H, m), 6.54 (2H, d, J=9.0 Hz), 6.70 (1H, br), 7.15 (2H, d, J=8.8 Hz), 7.24-7.30 (3H, m), 7.50 (1H, d, J=3.9 Hz), 7.80 (2H, d, J=8.3 Hz), 7.92 (1H, d, J=9.0 Hz)

[Step 4] 9.5 mg of the 6-acetyl-9-(4-chlorophenylamino)-7-methyl-3-tosyl-6,7,8,9-tetrahydro-3H-pyrrolo[3.2-f]quinoline were dissolved in methanol (1 mL) followed by adding 4 M aqueous sodium hydroxide solution (1 mL) and stirring for 30 minutes at 80° C. After allowing to cool to room temperature, the reaction liquid was neutralized by addition of saturated aqueous ammonium chloride solution followed by extracting with chloroform, washing the organic layer with saturated brine, dehydrating with anhydrous sodium sulfate and concentrating under reduced pressure. The resulting residue was purified by PLC (chloroform:methanol=20:1) to obtain 3.8 mg of the target compound in the form of a yellow oil (59.4%).

$^1$H-NMR (400 MHz, CDCl$_3$) δ: 1.15 (3H, br), 1.20-1.32 (1H, m), 2.18 (3H, s), 2.52-2.62 (1H, m), 4.02 (1H, br), 4.52-4.62 (1H, m), 5.07-5.21 (1H, m), 6.60 (2H, d, J=8.8 Hz), 6.56-6.63 (1H, m), 7.16 (2H, d, J=8.8 Hz), 7.14-7.29 (1H, m), 7.33 (1H, d, J=8.5 Hz), 8.26 (1H, br)

Example 8

Production of Cis-1-acetyl-9-[(4-chlorophenyl)amino]-7-methyl-6,7,8,9-tetrahydro-1H-imiazo[4,5-f]quinoline (Compound 8)

[Step 1] 3.2 g of a mixture of tert-butyl-5-amino-1H-benzo[d]imidazole-1-carboxylate and tert-butyl-6-amino-1H-benzo[d]imidazole-1-carboxylate and 671 mg of 1H-benzotriazole was dissolved in 90 mL of toluene followed by adding 6 mL of a toluene solution containing 0.9 mL of acetoaldehyde and stirring overnight at room temperature. Following completion of the reaction, 30 mL of heptane were added followed by stirring for 1 hour and concentrating under reduced pressure to obtain 5.2 g of a crude produce of tert-butyl-5-[1-(1H-benzo[d][1,2,3]triazol-1-yl)ethylamino]-1H-benzo[d]imidazole-1-carboxylate and tert-butyl-6-[1-(1H-benzo[d][1,2,3]triazol-1-yl)ethylamino]-1H-benzo[d]imidazole-1-carboxylate.

[Step 2] 400 mg of the mixture of tert-butyl-5-[1-(1H-benzo[d][1,2,3]triazol-1-yl)ethylamino]-1H-benzo[d]imidazole-1-carboxylate and tert-butyl-6-[1-(1H-benzo[d][1,2,3]triazol-yl)ethylamino]-1H-benzo[d]imidazole-1-carboxylate and 187 mg of benzyl vinyl carbamate were dissolved in 4.0 mL of toluene followed by adding 3 mg of p-toluenesulfonic acid monohydrate and stirring for 7 hours while heating at 70° C. Following completion of the reaction, the solution was neutralized by adding saturated aqueous sodium bicarbonate solution and extracted three times with chloroform. After washing with saturated brine and dehydrating with anhydrous sodium sulfate, the solution was concentrated under reduced pressure and the resulting residue was purified using silica gel chromatography (ethyl acetate:hexane=1:1) to obtain 75 mg of a mixture of cis-tert-butyl-9-benzyloxycarbonylamino-7-methyl-6,7,8,9-tetrahydro-1H-imidazo[4,5-f]quinoline-1-carboxylate and cis-tert-butyl-9-benzyloxycarbonylamino-7-methyl-6,7,8,9-tetrahydro-3H-imidazo[4,5-f]quinoline-3-carboxylate in the form of a brown oil (53%).

[Step 3] 75 mg of the mixture of cis-tert-butyl-9-benzyloxycarbonylamino-7-methyl-6,7,8,9-tetrahydro-1H-imidazo[4,5-f]quinoline-1-carboxylato and cis-tert-butyl-9-benzyloxycarbonylamino-7-methyl-6,7,8,9-tetrahydro-3H-imidazo[4,5-f]quinoline-3-carboxylate and 83 µL of pyridine were dissolved in 3 mL of dichloromethane followed by adding 37 µL of acetyl chloride while cooling with ice and stirring for 2.5 hours at room temperature. Following completion of the reaction, the solution was concentrated under reduced pressure and saturated aqueous sodium bicarbonate solution was added to the resulting residue followed by extracting three times with chloroform. After washing with saturated brine and dehydrating with anhydrous sodium sulfate, the solution was concentrated under reduced pressure and the resulting residue was purified using silica gel chromatography (ethyl acetate:hexane=1:1) to obtain 25 mg of a mixture of cis-tert-butyl-6-acetyl-9-benzyloxycarbonylamino-7-methyl-6,7,8,9-tetrahydro-1H-imidazo[4,5-f]-quinoline-1-carboxylate and cis-tert-butyl-6-acetyl-9-benzyloxycarbonylamino-7-methyl-6,7,8,9-tetrahydro-3H-imidazo[4,5-f]-quinoline-3-carboxylate in the form of a brown oil (30%).

[Step 4] 25 mg of the mixture of cis-tert-butyl-6-acetyl-9-benzyloxycarbonylamino-7-methyl-6,7,8,9-tetrahydro-1H-imidazo[4,5-f]-quinoline-1-carboxylate and cis-tert-butyl-6-acetyl-9-benzyloxycarbonylamino-7-methyl-6,7,8,9-tetrahydro-3H-imidazo[4,5-f]-quinoline-3-carboxylate were dissolved in 0.5 mL of methanol followed by adding 8 mg of 10% palladium hydroxide carbon and stirring for 18 hours in a hydrogen atmosphere at normal pressure and room temperature. Following completion of the reaction, the solution was filtered with celite and concentrated under reduced pressure. The resulting residue was purified using silica gel chromatography (methanol:chloroform 1:1) to obtain 9 mg of a mixture of cis-tert-butyl-6-acetyl-9-amino-7-methyl-6,7,8,9-tetrahydro-1H-imidazo[4,5-f]-quinoline-1-carboxylate and cis-tert-butyl-6-acetyl-9-amino-7-methyl-6,7,8,9-tetrahydro-3H-imidazo[4,5-f]-quinoline-3-carboxylate in the form of a colorless oil (50%).

[Step 5] 6 mg of the mixture of cis-tert-butyl-6-acetyl-9-amino-7-methyl-6,7,8,9-tetrahydro-1H-imidazo[4,5-f]-quinoline-1-carboxylate and cis-tert-butyl-6-acetyl-9-amino-7-methyl-6,7,8,9-tetrahydro-3H-imidazo[4,5-f]-quinoline-3-carboxylate and 4 mg of 4-chlorophenylboronic acid were dissolved in 0.2 ml, of dichloromethane followed by adding 6 mg of divalent copper acetate and 7 mL of triethylamine and stirring for 11 hours at room temperature in the presence of air. Following completion of the reaction, the solution was filtered with celite followed by addition of water and extracting three times with ethyl acetate. After washing with saturated brine and dehydrating with anhydrous sodium sulfate, the solution was concentrated under reduced pressure and the resulting residue was purified using silica gel chromatography (ethyl acetate:hexane=1:2) to obtain 8 mg of a mixture of cis-tert-butyl-6-acetyl-9-(4-chlorophenylamino)-7-methyl-6,7,8,9-tetrahydro-1H-imidazo[4,5-f]-quinoline-1-carboxylate and cis-tert-butyl-6-acetyl-9-(4-chlorophenylamino)-7-methyl-6,7,8,9-tetrahydro-3H-imidazo[4,5-f]-(quinoline-3-carboxylate in the form of a colorless oil (100%).

[Step 6] 7 mg of the mixture of cis-tert-butyl-6-acetyl-9-(4-chlorophenylamino)-7-methyl-6,7,8,9-tetrahydro-1H-imidazo[4,5-f]-quinoline-1-carboxylate and cis-tert-butyl-6-acetyl-9-(4-chlorophenylamino)-7-methyl-6,7,8,9-tetrahydro-3H-imidazo[4,5-f]-quinoline-3-carboxylate were dissolved in 0.2 mL of dichloromethane followed by adding 1 mL of an ethyl acetate solution of 4 N hydrochloric acid while cooling with ice and stirring for 1.5 hours at room temperature. Following completion of the reaction, the solution was neutralized with saturated aqueous sodium bicarbonate solution and extracted three times with chloroform. After washing with saturated brine and dehydrating with anhydrous sodium sulfate, the solution was concentrated under reduced pressure and the resulting residue was washed with diethyl ether to obtain 8 mg of the target compound in the form of a white solid (91%).

$^1$H-NMR (400 MHz, CDCl$_3$) δ: 1.20 (3H, d, J=6.3 Hz), 1.65-1.73 (1H, m), 2.15 (3H, s), 2.87 (1H, ddd, J=5.1, 8.2 12.8 Hz), 4.66 (1H, dd, J=4.9, 11.0 Hz), 4.93-5.04 (1H, m), 7.40 (1H, d, J=8.6 Hz), 7.62-7.70 (5H, m), 8.4 (1H, s)

Example 9

Production of cis-7-acetyl-10-(4-chlorophenylamino)-8-methyl-7,8,9,10-tetrahydro-3H-pyrano[3,2-f]-quinolin-3-one (Compound 9)

[Step 1] 840 mg of 5-aminocoumarin and 621 mg of 1H-benzotriazole were dissolved in 100 mL of toluene followed by adding 3 mL of a toluene solution containing 0.3 mL of acetoaldehyde and stirring overnight at room temperature. Following completion of the reaction, 30 ml of heptane were added followed by stirring for 1 hour and filtering to obtain 1.6 g of a crude product of 6-(1-(1H-benzo[d][1,2,3]triazol-1-yl)ethylamino)-2H-chromen-2-one.

[Step 2] 300 mg of the 6-(1-(1H-benzo[d][1,2,3]triazol-1-yl)ethylamino)-2H-chromen-2-one and 174 mg of benzyl vinyl carbamate were dissolved in 3.5 mL of toluene followed by adding 2 mg of p-toluenesulfonic acid monohydrate and stirring for 2 hours while heating at 70° C. Following completion of the reaction, the solution was neutralized by adding saturated aqueous sodium bicarbonate solution and then extracted three times with chloroform. After washing with saturated brine and dehydrating with anhydrous sodium sulfate, the solution was concentrated under reduced pressure and the resulting residue was purified by recrystallization (ethyl acetate-hexane) to obtain 231 mg of cis-benzyl-8-methyl-3-oxo-7,8,9,10-tetrahydro-3H-pyrano[3,2-f]-quinolin-10-yl carbamate in the form of a yellow solid (65%).

[Step 3] 226 mg of the cis-benzyl-8-methyl-3-oxo-7,8,9,10-tetrahydro-3H-pyrano[3,2-f]-quinolin-10-yl carbamate and 0.15 mL of pyridine were dissolved in 10 of dichloromethane followed by adding 66 µL of acetyl chloride while cooling with ice and stirring for 1 hour at room temperature. Following completion of the reaction, the solution was concentrated under reduced pressure and saturated aqueous sodium bicarbonate solution was added to the resulting residue followed by extracting three times with chloroform. After washing with saturated brine and dehydrating with anhydrous sodium sulfate, the solution was concentrated under reduced pressure and the resulting residue was purified using silica gel chromatography (ethyl acetate:hexane=1:1) to obtain 250 mg of cis-benzyl-7-acetyl-8-methyl-3-oxo-7,8,9,10-tetrahydro-3H-pyrano[3,2-f]-quinolin-10-yl carbamate in the form of a yellow solid (99%).

[Step 4] 170 mg of the cis-benzyl-7-acetyl-8-methyl-3-oxo-7,8,9,10-tetrahydro-3H-pyrano[3,2-f]-quinolin-10-yl carbamate and 132 mg of ammonium formate were dissolved in 5 mL of ethanol followed by adding 51 mg of 10% palladium carbon and stirring for 7.5 hours in a hydrogen atmosphere at normal pressure and room temperature. Following completion of the reaction, the solution was filtered with celite and then concentrated under reduced pressure. The resulting residue was neutralized with saturated aqueous sodium bicarbonate solution followed by extracting three times with chloroform. After washing with saturated brine and dehydrating with anhydrous sodium sulfate, the solution was concentrated under reduced pressure to obtain 23 mg of cis-benzyl-7-acetyl-10-amino-8-methyl-7,8,9,10-tetrahydro-3H-pyrano[3,2-f]-quinolin-3-one in the form of a colorless oil (20%).

[Step 5] 22 mg of the cis-benzyl-7-acetyl-10-amino-8-methyl-7,8,9,10-tetrahydro-3H-pyrano[3,2-f]-quinolin-3-one and 19 mg of 4-chlorophenylboronic acid were dissolved in 10 mL of dichloromethane followed by adding 29 mg of divalent copper acetate and 34 µL of triethylamine and stirring for 18 hours at room temperature in the presence of air. Following completion of the reaction, the solution was filtered with celite and water was added followed by extracting three times with ethyl acetate. After washing with saturated brine and dehydrating with anhydrous sodium sulfate, the solution was concentrated under reduced pressure and the resulting residue was purified using silica gel chromatography (ethyl acetate:hexane=1:1) to obtain 7 mg of the target compound in the form of a yellow solid (23%).

$^1$H-NMR (400 MHz, CDCl$_3$) δ: 1.25-1.31 (4H, m), 2.18-2.36 (4H, m), 3.85 (1H, d, J=7.8 Hz), 4.74-4.84 (1H, m), 6.33 (1H, d, J=10.0 Hz), 6.60 (2H, d, J=6.8 Hz), 7.22 (2H, d, J=6.8 Hz), 7.28-7.30 (2H, m), 7.74-7.92 (1H, brd)

Example 10

Production of cis-1-[8-(4-chlorophenylamino)-6-methyl-7,8-dihydro-[1,3]dioxolo[4,5-g]quinolin-5(6H)-yl]ethanone (Compound 10)

[Step 1] 10 mL of a toluene suspension containing 1.4 g (10 mmol) of benzo[d][1,3]dioxol-5-amine were added to 10 mL of a toluene suspension containing 1.2 g (10 mmol) of benzotriazole followed by stirring. 10 mL of a toluene solution containing 0.62 mL (11 mmol) of acetoaldehyde were dropped therein followed by stirring for 18 hours at room temperature. Following completion of the reaction, 10 mL of n-hexane were added followed by filtering out the solid. The solid was washed with n-hexane and dried under reduced pressure to obtain 2.7 g of N-[1-(1H-benzo[d][1,2,3]triazol-1-yl)ethyl]benzo[d][1,3]dioxol-5-amine in the form of a pale brown solid (94%).

[Step 2] 484 mg (1.7 mmol) of the N-[1-(1H-benzo[d][1,2,3]triazol-1-yl)ethyl]benzo[d][1,3]dioxol-5-amine, 304 mg (1.7 mmol) of benzyl vinyl carbamate and 3.4 mg (0.017 mmol) of p-toluenesulfonic acid were suspended in 10 mL of toluene followed by stirring for 2 hours at 70° C. Following completion of the reaction, the reaction liquid was washed with saturated aqueous sodium bicarbonate solution, the washing was extracted with ethyl acetate, and the organic layers were combined and washed with saturated brine. This was then dehydrated with anhydrous sodium sulfate, concentrated under reduced pressure, and the resulting residue was purified by silica gel column chromatography (n-hexane:ethyl acetate=3:1) to obtain benzyl-6-methyl-5,6,7,8-tetrahydro[1,3]dioxolo[4,5-g]quinolin-8-yl carbamate in the form of a yellowish-brown oil.

[Step 3] 675 mg (approx. 1.98 mmol) of the benzyl-6-methyl-5,6,7,8-tetrahydro[1,3]dioxolo[4,5-g]quinolin-8-yl carbamate were dissolved in 15 mL of dichloromethane followed by adding 313 mg (4.0 mmol) of pyridine. 234 mg (3.0 mmol) of acetyl chloride were further added followed by stirring for 30 minutes at room temperature. Following completion of the reaction, aqueous hydrochloric acid (1 mol/L) was added followed by extraction with chloroform. The organic phase was washed with water and then dehydrated with anhydrous sodium sulfate. The solution was concentrated under reduced pressure and the resulting residue was purified by silica gel column chromatography (n-hexane:ethyl acetate 2:1) to obtain 367 mg of benzyl-5-acetyl-6-methyl-5,6,7,8-tetrahydro-[1,3]dioxolo[4,5-g]quinolin-8-yl carbamate in the form of a pale brown oil (56%, 2 steps).

$^1$H-NMR (270 MHz, CDCl$_3$) δ: 1.07-1.13 (4H, m), 1.53-1.55 (1H, m), 1.54 (1H, s), 2.11 (3H, s), 2.49-2.62 (1H, m), 4.47-4.61 (1H, m), 4.83 (2H, d, J=9.6 Hz), 5.17 (2H, s), 5.98 (2H, s), 6.64 (1H, s), 6.74 (1H, s), 7.30-7.46 (5H, m)

[Step 4] 375 mg (0.96 mmol) of the benzyl-5-acetyl-6-methyl-5,6,7,8-tetrahydro-[1,3]dioxolo[4,5-g]quinolin-8-yl carbamate were dissolved in 4 mL of ethanol followed by adding 242 mg (3.84 mmol) of ammonium formate and further adding 100 mg of palladium carbon. The system was replaced with hydrogen followed by stirring for 1 hour. Following completion of the reaction, the reaction liquid was filtered with celite and the filtrate was concentrated under reduced pressure. The residue was dissolved in chloroform, washed with saturated aqueous sodium bicarbonate solution and dehydrated with anhydrous sodium sulfate. The solution was concentrated under reduced pressure to obtain 225 mg (including impurities) of 1-(8-amino-6-methyl-7,8-dihydro-[1,3]dioxolo[4.5-g]quinolin-5(6H)-yl)ethanone in the form of a yellow oil.

[Step 5] 40 mg (0.16 mmol) of the 1-(8-amino-6-methyl-7,8-dihydro-[1,3]dioxolo[4.5-g]quinolin-5(6H)-yl)ethanone, 38 mg (0.24 mmol) of 4-chlorophenylboronic acid, 59 mg (0.33 mmol) of copper (II) acetate, 49 mg (0.48 mmol) of triethylamine and 2 mL of dichloromethane suspension containing 30 mg of molecular sieve (4A) were vigorously stirred for 2 days. Following completion of the reaction, aqueous ammonium chloride solution was added followed by extraction with chloroform. The extract was washed with water and the organic layer was dehydrated with anhydrous sodium sulfate. The solution was concentrated under reduced pressure and the resulting residue was purified by silica gel column chromatography (n-hexane:ethyl acetate=1:1) to obtain 18 mg of cis-1-[8-(4-chlorophenylamino)-6-methyl-7,8-dihydro[1,3]dioxolo[4,5-g]quinolin-5(6H)-yl]ethanone in the form of a yellow oil (29%, 2 steps).

$^1$H-NMR (270 MHz, CDCl$_3$) δ: 1.12 (3H, d, J=6.3 Hz), 1.23-1.29 (1H, m), 2.18 (3H, s), 2.55-2.68 (1H, m), 3.81 (1H, d, J=6.6 Hz), 3.95-4.07 (1H, m), 4.93 (1H, brs), 5.96 (2H, s), 6.52 (2H, dd, J=6.6, 2.3 Hz), 6.65 (1H, brs), 6.73 (1H, s), 7.13 (2H, dd, J=6.8, 2.1 Hz)

[Step 6] 29 mg of the cis-1-[8-(4-chlorophenylamino)-6-methyl-7,8-dihydro[1,3]-dioxolo[4,5-g]quinolin-5(6H)-yl]ethanone were dissolved in 2 mL of ethyl acetate followed by adding 0.08 mL of hydrochloric acid/ethyl acetate (4 mol/L) and filtering the precipitated solid. The solid was washed with ethyl acetate and dried under reduced pressure to obtain 21 mg of the target compound in the form of a yellow crystalline powder.

$^1$H-NMR (270 MHz, CDCl$_3$) δ: 1.01 (3H, d, J=5.9 Hz), 1.07-1.15 (1H, m), 2.07 (3H, s), 4.69 (1H, brs), 5.99 (2H, s), 6.54 (1H, s), 6.63 (2H, d, J=8.9 Hz), 7.03 (1H, s), 7.11 (2H, d, J=8.9 Hz)

Example 11

Production of 6-acetyl-9-[(4-chlorophenyl)amino]-7-methyl-2,3,6,7,8,9-hexahydro-[1,4]dioxano[2,3-g]quinoline (Compound 11)

[Step 1] 1.0 g of 1,4-benzodioxane-6-amine and 788 mg of 1H-benzotriazole were dissolved in 40 mL of toluene followed by adding 5 mL of a toluene solution containing 0.42 mL of acetoaldehyde and stirring overnight at room temperature. Following completion of the reaction, after adding 20 mL of heptane and stirring for 1 hour, the solution was filtered to obtain 1.6 g a crude product of N-[1-(1H-benzo[d][1,2,3]triazol-1-yl)ethyl]-2,3-dihydrobenzo[b][1,4] dioxane-6-amine.

[Step 2] 300 mg of the N-[1-(1H-benzo[d][1,2,3]triazol-1-yl)ethyl]-2,3-dihydrobenzo[b][1,4]dioxane-6-amine and 179 mg of benzyl vinyl carbamate were dissolved in 3.5 mL of toluene followed by adding 2 mg of p-toluenesulfonic acid monohydrate and stirring for 2 hours at 70° C. Following completion of the reaction, the solution was neutralized with saturated aqueous sodium bicarbonate solution and extracted three times with chloroform. After washing with saturated brine and dehydrating with anhydrous sodium sulfate, the solution was concentrated under reduced pressure and the resulting residue was purified using silica gel chromatography (ethyl acetate:hexane=1:3) to obtain 320 mg of cis-benzyl-7-methyl-2,3,6,7,8,9-hexahydro-[1,4]dioxano[2,3-g]-quinolin-9-yl carbamate in the form of a brown amorphous substance.

[Step 3] 320 mg of the cis-benzyl-7-methyl-2,3,6,7,8,9-hexahydro-[1,4]dioxano[2,3-g]-quinolin-9-yl carbamate and 0.22 mL of pyridine were dissolved in 7 mL of dichloromethane followed by adding 96 μL of acetyl chloride while cooling with ice and stirring overnight at room temperature. Following completion of the reaction, the solution was concentrated under reduced pressure, and saturated aqueous sodium bicarbonate solution was added to the resulting residue followed by extracting three times with chloroform. After washing with saturated brine and dehydrating with anhydrous sodium sulfate, the solution was concentrated under reduced pressure and the resulting residue was purified using silica gel chromatography (ethyl acetate:hexane=1:1) to obtain 180 mg of cis-benzyl-6-acetyl-7-methyl-2,3,6,7,8,9-hexahydro[1,4] dioxano[2,3-g]-quinolin-9-yl carbamate in the form of a brown amorphous substance.

[Step 4] 180 mg of the cis-benzyl-6-acetyl-7-methyl-2,3,6,7,8,9-hexahydro[1,4]dioxano[2,3-g]-quinolin-9-yl carbamate and 86 mg of the ammonium formate were dissolved in 5 mL of ethanol followed by adding 54 mg of 10% palladium carbon and stirring for 2 hours in a hydrogen atmosphere at normal pressure and room temperature. Following completion of the reaction, the solution was filtered with celite and concentrated under reduced pressure. The resulting residue was neutralized with saturated aqueous sodium bicarbonate solution followed by extracting three times with chloroform. After washing with saturated brine and dehydrating with anhydrous sodium sulfate, the solution was concentrated under reduced pressure to obtain 39 mg of cis-6-acetyl-9-amino-7-methyl-2,3,6,7,8,9-hexahydro-[1,4]dioxano[2,3-g]quinoline in the form of a brown oil (33%).

[Step 5] 15 mg of the cis-6-acetyl-9-amino-7-methyl-2,3,6,7,8,9-hexahydro-[1,4]dioxano[2,3-g]quinoline and 13 mg of 4-chlorophenylboronic acid were dissolved in 0.3 mL of dichloromethane followed by adding 21 mg of divalent copper acetate and 24 μL of triethylamine and stirring overnight at room temperature in the presence of air. Following completion of the reaction, the solution was filtered with celite followed by the addition of water and extracting three times with ethyl acetate. After washing with saturated brine and dehydrating with anhydrous sodium sulfate, the solution was concentrated under reduced pressure and the resulting residue was purified using silica gel chromatography (ethyl acetate:hexane=1:1) to obtain 8 mg of the target compound in the form of a white solid (38%).

$^1$H-NMR (400 MHz, CDCl$_3$) δ: 1.08-1.27 (4H, m), 2.18 (3H, s), 2.59 (1H, ddd, J=4.2, 8.5, 12.3 Hz), 4.02-4.09 (1H, m), 4.21-4.29 (4H, m), 4.80-4.98 (1H, m), 6.53 (2H, d, J=6.6 Hz), 6.64-6.70 (1H, brs), 6.73 (1H, s), 7.12 (2H, d, J=6.6 Hz)

Example 12

Production of cis-6-acetyl-9-(4-chlorophenylamino)-7-methyl-6,7,8,9-tetrahydro-2H-[1,4]oxazino[2,3-g]quinolin-3-(4H)-one (Compound 12)

[Step 1] 6-(1-(1H-2-benzo[d][1,2,3]triazol-1-yl)ethylamino)-2H-benzo[b][1,4]oxazin-3(4H)-one was obtained as a crude product in the same manner as Step 2 of Example 5 by using as raw material 6-amino-2H-benzo[b][1,4]oxazin-3 (4H)-one. Benzyl-7-methyl-3-oxo-3,4,6,7,8,9-hexahydro-2H-[1,4]oxazino[2,3-g]quinolin-9-yl carbamate was obtained as a crude product by treating this crude product in the same manner as Step 2 of Example 5. 149 mg of a crude form of benzyl-6-acetyl-7-methyl-3-oxo-3,4,6,7,8,9-hexahydro-2H-[1,4]oxazino[2,3-g]quinolin-9-yl carbamate were obtained by treating this crude product in the same manner as Step 3 of Example 5 40.2 mg of 6-acetyl-9-amino-7-methyl-6,7,8,9-tetrahydro-2H-[1,4]oxazino[2,3-g]quinolin-3(4H)-one were obtained in the form of a yellow oil by using the benzyl-6-acetyl-7-methyl-3-oxo-3,4,6,7,8,9-hexahydro-2H-[1,4]oxazino[2,3-g]quinolin-9-yl carbamate as a raw material and treating in the same manner as Step 4 of Example 5 (8.3%).

$^1$H-NMR (400 MHz, CDCl$_3$) δ: 1.02-1.09 (4H, m), 2.12 (3H, brs), 2.47-2.57 (1H, m), 3.64-3.72 (1H, m), 4.63 (2H, brs), 4.82 (1H, br), 6.67 (1H, br), 7.11 (1H, brs), 5.46 (1H, br)

[Step 2] 19.0 mg of the target compound were obtained in the form of a pale yellow solid by using the 6-acetyl-9-amino-7-methyl-6,7,8,9-tetrahydro-2H-[1,4]oxazino[2,3-g]quinolin-3(4H)-one as a raw material and treating in the same manner as Step 5 of Example 5 (33.7%).

$^1$H-NMR (400 MHz, CDCl$_3$) δ: 1.05 (3H, d, J=6.1 Hz), 1.06-1.16 (1H, m), 1.88 (3H, brs), 2.50 (1H, ddd, J=12.3, 8.3, 4.3 Hz), 3.67 (1H, dd, J=12.0, 3.9 Hz), 4.68-4.84 (3H, m), 6.15 (1H, br), 7.19 (1H, s), 7.24 (2H, d, J=8.5 Hz), 7.53 (2H, d, J=8.8 Hz)

Test Examples

Compounds produced using the methods described in the examples were used in the test examples.

Test Example 1

<Materials and Methods>

Human hepatocellular carcinoma cell line HepG2 was inoculated in aliquots of 5×10$^4$ cells each into each of the wells of a 48-well plate using minimum essential medium (MEM, Sigma) containing 10% fetal bovine serum. On the following day, the medium was replaced with Dulbecco's Modified Eagle Medium (DMEM, Sigma) not containing phenol red but containing 10% fetal bovine serum followed by the addition of a test compound dissolved in DMSO to a final concentration of 3 μM or 10 and bringing to a final media volume of 400 μl per well. After incubating for 48 hours in a CO$_2$ incubator having an oxygen concentration of 4%, the culture supernatant was recovered. The concentration of EPO in the culture supernatant was measured immediately using an ELISA kit (Roche Diagnostics). The procedure used complied with that described in the instructions.

The produced amount of EPO derived from each compound was determined based on a value of 100% for the amount of EPO produced in a non-stimulated state in the absence of addition of a compound (% of control). The results are shown in Tables 3 and 4.

TABLE 3

| Compound No. | % of Control (3 μM) |
| --- | --- |
| 1 | 416 |
| 2 | 392 |
| 3 | 153 |
| 4 | 137 |

TABLE 4

| Compound No. | % of Control (10 μM) |
| --- | --- |
| 5 | 183 |
| 7 | 137 |
| 8 | 104 |
| 9 | 116 |
| 10 | 191 |
| 11 | 190 |
| 12 | 103 |

<Results>

Addition of the test compounds at a final concentration of 3 μm was observed to promote production of EPO by a maximum of 416% (Compound 1) (see Table 3). On the basis thereof, these compounds clearly demonstrated an action that promotes production of EPO, and were determined to be useful as anemia therapeutic agents.

Test Example 2

<Materials and Methods>

Human proerythroblast cell line K562 (acquired from ATCC) was inoculated in aliquots of 1×10$^5$ cells/mL into each of the wells of a 24-well plate using complete medium (RPMI-1640 medium containing 10% fetal bovine serum), followed by the addition of the test compounds at a final concentration of 6 μM and incubating for 3 days in a CO$_2$ incubator (37° C., 5% CO$_2$). Culturing was continued for an additional 3 days after replacing the medium. The cells were then collected and counted followed by unifying to a cell count of 3×10$^5$ cells and determining the amount of hemoglobin produced in the cells by measuring the fluorescence of the porphyrin ring. Namely, the cells collected by centrifugation were suspended in 500 μL of 2 M oxalic acid, and boiled for 30 minutes and allowed to cool, followed by measuring fluorescence intensity with a fluorescent microplate reader (Spectra MAX Gemini EM, MDC Japan, Inc.) (Em: 400 am, Ex: 603 nm). The amount of hemoglobin induced to be produced by each compound was determined based on a value of 100% for the amount of hemoglobin produced in a non-stimulated state in the absence of addition of a compound (% of control). The results are shown in Table 5.

TABLE 5

| Compound No. | % of Control (6 μM) |
| --- | --- |
| 1 | 197 |
| 2 | 249 |
| 3 | 105 |
| 4 | 135 |
| 7 | 436 |
| 8 | 185 |
| 9 | 166 |
| 10 | 520 |
| 11 | 302 |

<Results>

The addition of the test compounds at a concentration of 6 μM was observed to promote production of hemoglobin by a maximum of 520% (Compound 10) (see Table 5). Thus, the compounds of the present invention were clearly determined to demonstrate action that promotes maturation from proerythroblasts into erythrocytes and promotes production of hemoglobin.

On the basis of the above results, the fused piperidine compound represented by general formula (1) of the present invention, a salt thereof, or a solvate thereof was demonstrated to have action that promotes EPO production and action that promotes hemoglobin production, thereby making it useful as an anemia therapeutic agent.

Industrial Applicability

The present invention provides a low molecular weight anemia preventive and/or therapeutic agent capable of oral administration and having superior EPO production-promoting action and/or hemoglobin production-promoting action based on finding for the first time that the fused piperidine compound represented by general formula (1), a salt thereof, or a solvate thereof has superior EPO production-promoting action and/or hemoglobin production-promoting action. The present invention provides a novel, low molecular weight anemia preventive and/or therapeutic agent that is useful in the pharmaceutical industry and has industrial applicability.

The invention claimed is:

1. A fused piperidine compound represented by the following general formula (1):

[Chemical Formula 1]

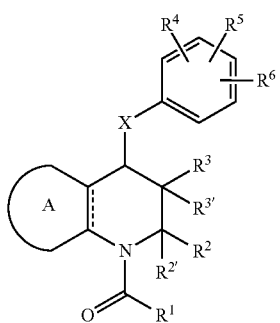

(1)

wherein, ring A represents a $C_{10-14}$ aryl group or 5- to 10-membered heterocyclic group, X represents N—$R^7$, a sulfur atom or an oxygen atom, where $R^7$ represents a hydrogen atom or a $C_{1-6}$ alkyl group, $R^1$, $R^2$, $R^{2'}$, $R^3$ and $R^{3'}$ independently represent a hydrogen atom, $C_{1-6}$ alkyl group or $C_{3-6}$ cycloalkyl group, and $R^4$, $R^5$ and $R^6$ independently represent a hydrogen atom or halogen atom, a salt thereof, or a solvate thereof.

2. The compound according to claim 1, wherein the ring A moiety is selected from the group consisting of the following formulas:

[Chemical Formula 2]

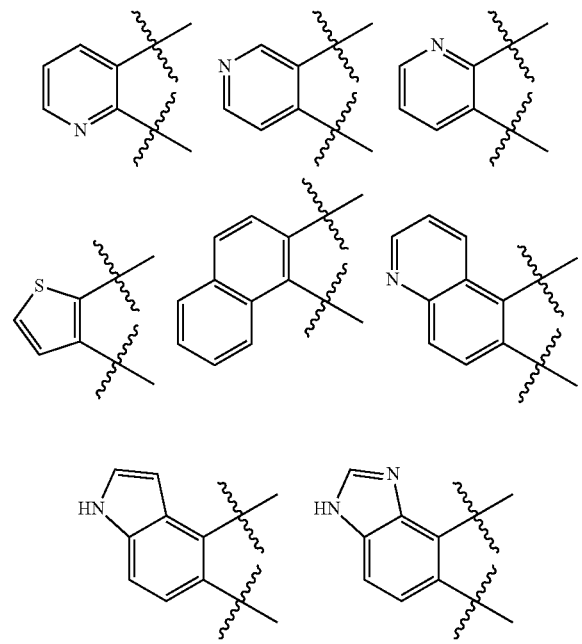

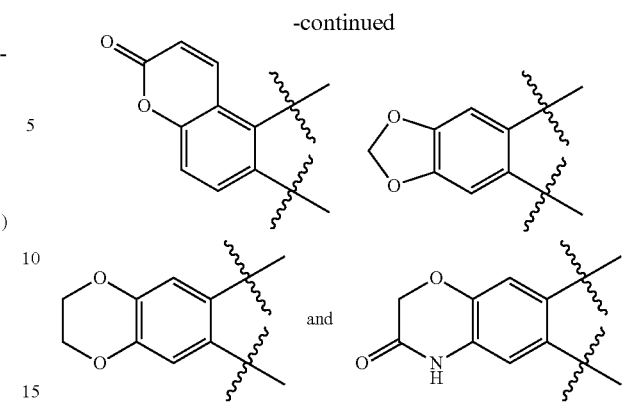

and a salt thereof, or a solvate thereof.

3. The compound according to claim 1, wherein the compound represented by general formula (1) is selected from the group consisting of:
   1-acetyl-4-[(4-chlorophenyl)amino]-2-methyl-3,4-dihydro-2H-[1,8]-naphthyridine (Compound 1),
   1-acetyl-4-[(4-chlorophenyl)amino]-2-methyl-3,4-dihydro-2H-[1,6]-naphthyridine (Compound 2),
   1-acetyl-4-[(4-chlorophenyl)amino]-2-methyl-3,4-dihydro-2H-[1,5]-naphthyridine (Compound 3),
   1-(7-(4-chlorophenylamino)-5-methyl-6,7-dihydrothieno[3,2-b]pyridine-4(5H)-yl)ethanone (Compound 4),
   1-acetyl-4-[(4-chlorophenyl)amino]-2-methyl-1,2,3,4-tetrahydro-benzo[h]quinoline (Compound 5),
   1-[1-(4-chlorophenylamino)-3-methyl-2,3-dihydro-4,7-phenanthroline-4-(1H)-yl]ethanone (Compound 6),
   6-acetyl-9-(4-chlorophenylamino)-7-methyl-6,7,8,9-tetrahydro-3H-pyrrolo[3,2-f]quinoline (Compound 7),
   1-acetyl-9-[(4-chlorophenyl)amino]-7-methyl-6,7,8,9-dihydro-1H-imidazo[4,5-f]quinoline (Compound 8),
   7-acetyl-10-[(4-chlorophenyl)amino]-8-methyl-7,8,9,10-tetrahydro-3H-pyrano[3,2-f]-quinolin-3-one (Compound 9),
   1-[8-(4-chlorophenylamino)-6-methyl-7,8-dihydro-[1,3]dioxolo[4,5-g]quinolin-5(6H)-yl]ethanone (Compound 10),
   6-acetyl-9-[(4-chlorophenyl)amino]-7-methyl-2,3,6,7,8,9-hexahydro-[1,4]dioxano[2,3-g]-quinoline (Compound 11), and
   6-acetyl-9-(4-chlorophenylamino)-7-methyl-6,7,8,9-tetrahydro-2H-[1,4]oxazino[2,3-g]quinolin-3(4H)-one (Compound 12), or a salt thereof, or a solvate thereof.

4. A pharmaceutical composition comprising one or more compounds according to claim 1, or a salt thereof, or a solvate thereof, and a pharmaceutically acceptable carrier.

5. The pharmaceutical composition according to claim 4 for promoting production of EPO.

6. The pharmaceutical composition according to claim 4, for promoting the production of hemoglobin.

7. The pharmaceutical composition according to claim 4, for the prevention and/or treatment of anemia.

8. An EPO production promoter having as an active ingredient thereof the compound according to claim 1, a salt thereof, or a solvate thereof.

9. A hemoglobin production promoter having as an active ingredient thereof the compound according to claim 1, a salt thereof, or a solvate thereof.

10. An anemia preventive and/or therapeutic agent having as an active ingredient thereof the compound according to claim 1, a salt thereof, or a solvate thereof.

11. A method of promoting production of EPO, comprising administering an effective amount of the compound according to claim 1, a salt thereof or a solvate thereof, to a patient requiring promotion of EPO production.

12. A method of promoting production of hemoglobin, comprising administering an effective amount of the compound according to claim 1, a salt thereof or a solvate thereof, to a patient requiring promotion of hemoglobin production.

13. A method of preventing and/or treating anemia, comprising administering an effective amount of the compound according to claim 1, a salt thereof or a solvate thereof, to an anemia patient.

* * * * *